(12) United States Patent
Choi et al.

(10) Patent No.: US 11,000,481 B2
(45) Date of Patent: May 11, 2021

(54) COMPOSITE PREPARATION OF MOSAPRIDE AND RABEPRAZOLE

(71) Applicant: KOREA UNITED PHARM. INC., Sejong (KR)

(72) Inventors: Youn Woong Choi, Ansan-si (KR); Hee Yong Song, Sejong (KR); Dae-Chul Ha, Sejong (KR); Byung Jin Kim, Sejong (KR)

(73) Assignee: KOREA UNITED PHARM. INC., Sejong (KR)

( * ) Notice: Subject to any disclaimer, the term of this patent is extended or adjusted under 35 U.S.C. 154(b) by 268 days.

(21) Appl. No.: 15/739,532

(22) PCT Filed: Jun. 27, 2016

(86) PCT No.: PCT/KR2016/006862
§ 371 (c)(1),
(2) Date: Dec. 22, 2017

(87) PCT Pub. No.: WO2016/209061
PCT Pub. Date: Dec. 29, 2016

(65) Prior Publication Data
US 2018/0177731 A1    Jun. 28, 2018

(30) Foreign Application Priority Data

Jun. 26, 2015 (KR) .................. 10-2015-0091193
Nov. 24, 2015 (KR) .................. 10-2015-0164795

(51) Int. Cl.
| | |
|---|---|
| *A61K 9/24* | (2006.01) |
| *A61K 31/4439* | (2006.01) |
| *A61K 31/5375* | (2006.01) |
| *A61K 9/48* | (2006.01) |
| *A61K 9/50* | (2006.01) |
| *A61K 47/38* | (2006.01) |
| *A61K 9/20* | (2006.01) |
| *A61K 9/28* | (2006.01) |

(52) U.S. Cl.
CPC ............ *A61K 9/209* (2013.01); *A61K 9/2095* (2013.01); *A61K 9/2806* (2013.01); *A61K 9/4808* (2013.01); *A61K 9/4891* (2013.01); *A61K 9/5084* (2013.01); *A61K 31/4439* (2013.01); *A61K 31/5375* (2013.01); *A61K 47/38* (2013.01); *A61K 9/2054* (2013.01); *A61K 9/2846* (2013.01); *A61K 9/5078* (2013.01)

(58) Field of Classification Search
CPC .... A61K 9/209; A61K 9/2095; A61K 9/2806; A61K 9/4808; A61K 9/4891; A61K 9/5084; A61K 31/4439; A61K 31/5375
See application file for complete search history.

(56) References Cited

U.S. PATENT DOCUMENTS

| | | | | |
|---|---|---|---|---|
| 6,132,771 | A * | 10/2000 | Depui ............... | A61K 31/445 424/468 |
| 7,736,667 | B2 | 6/2010 | Berner et al. | |
| 2009/0280175 | A1 * | 11/2009 | Chauhan ............ | A61K 9/2886 424/472 |

FOREIGN PATENT DOCUMENTS

| | | |
|---|---|---|
| EA | 200800618 | 6/2008 |
| EA | 012261 B1 | 8/2009 |
| EP | 2 407 162 A1 | 1/2012 |
| JP | H 11-501949 A | 2/1999 |
| JP | 2007-137842 A | 6/2007 |
| JP | 2010-517937 A | 5/2010 |
| JP | 2018-518521 A | 7/2018 |
| KR | 10-2011-0103113 A | 9/2011 |
| KR | 10-2014-0113542 A | 9/2014 |
| RU | 2478375 C2 | 4/2013 |
| WO | WO 2006/011159 A2 | 2/2006 |
| WO | WO 2014-142616 A1 | 9/2014 |
| WO | WO 2014142616 * | 9/2014 |
| WO | WO 2015-014766 A1 | 2/2015 |

OTHER PUBLICATIONS

Kim et al. WO 2014/142616, published: Sept. 189, 2014, english machine translation obtained on Sep. 11, 2020. (Year: 2014).*
International Search Report dated Sep. 23, 2016 in connection with PCT International Application No. PCT/KR2015/006862.
Notice of Allowance dated Apr. 20, 2018 by the Korean Intellectual Property Office in connection with related Korean Patent Application No. 10-2016-0080449 including an English language translation.
Motor Leela Keerthi et al., "Pharmaceutical Mini-Tablets, its Advantages, Formulation Possibilities and General Evaluation Aspects: A Review", Int. J. Pharm. Sci. Rev. Res., 28(1), Sep.-Oct. 2014, Article No. 40, pp. 214-221.
Office Action dated Nov. 6, 2018 by the Japanese Patent Office in connection with related Japanese Patent Application No. 2017-567212.
Office Action dated Oct. 31, 2018 by the Russian Patent Office in connection with related Russian Patent Application No. 2018100755/04.
Mar. 21, 2019 Office Action issued by the Russian Patent Office in connection with related Russian Patent Application No. 2018100755/04.
Kondratieva, T.S. (1991), Tekhnologiya lekarstvennykh form. T.1, M:Medicina p. 72-73, including English translation of Abstract.
Office Action dated Sep. 1, 2020 by the Japanese Patent Office in connection with Japanese Patent Application No. 2019-170652.
Office Action dated Jan. 5, 2021 by the Japanese Patent Office in connection with Japanese Patent Application No. 2017-567212.

* cited by examiner

*Primary Examiner* — Genevieve S Alley
(74) *Attorney, Agent, or Firm* — John P. White

(57) ABSTRACT

The present invention relates to a composite preparation with various dosage forms comprising mosapride and rabeprazole.
The composite preparation prepared according to the present invention allows rapid release of a drug without deteriorating its release by an interaction between mosapride and rabeprazole, thus exhibiting an improved drug release rate and bioavailability, while having excellent product stability and being capable of significantly lowering the amount of the excipient. Accordingly, the composite preparation of the present invention can improve patients' drug compliance due to the size of its dosage form.

5 Claims, 3 Drawing Sheets

COMPOSITE PREPARATION OF MOSAPRIDE AND RABEPRAZOLE

CROSS-REFERENCE TO RELATED APPLICATIONS

This application is a § 371 national stage of PCT International Application No. PCT/KR2016/006862, filed Jun. 27, 2016, claiming priority of Korean Patent Applications Nos. KR 10-2015-0164795, filed Nov. 24, 2015 and KR 10-2015-0091193, Jun. 26, 2015, the contents of each of which are hereby incorporated by reference into the application.

TECHNICAL FIELD

The present invention relates to a composite preparation with various dosage forms containing mosapride and rabeprazole

Background Art

Mosapride, which is a selective serotonin 5-hydroxytryptamine 4 (hereinafter, "5-HT4") receptor agonist, is a drug that promotes the release of acetylcholine at the nerve end by selectively stimulating only the serotonin 5-T4 receptors present in the myenteric plexus, in which the acetylcholine contracts the smooth muscle of the digestive tract and promotes digestive tract motility, thereby showing excellent efficacy in the treatment of diabetic gastropathy, dyspepsia, gastritis, and gastroesophageal reflux disease. Mosapride is a safe drug which is free from the risk of arrhythmia or sudden cardiac death caused by the prolongation of QT interval shown in cisapride (i.e., a non-selective 5-HT4 receptor agonist) and has no side effects such as central nervous system (CNS) side effects (extrapyramidal symptoms) or hyperprolactinemia (lactation and gynecomastia).

Meanwhile, rabeprazole, which is a benzimidazole derivative that inhibits gastric acid secretion, is known as a proton pump inhibitor (PPI) that inhibits $H^+/K^+$ ATPase and thereby inhibits gastric acid secretion on the surface of the parietal cells of the gastric mucosa for acid secretion. Furthermore, rabeprazole induces inhibition of basal acid secretion and acid secretion by stimulation and is thus attracting attention as a therapeutic agent for peptic ulcer, duodenal ulcer, etc.

Although composite preparations of two components having similar drug efficacy have advantages in that they can replace combination therapies, improve drug compliance of patients, and be more economical than administering each agent in combination, there is a concern that a change in dissolution pattern or side effects in the body may occur due to an interaction between drugs. However, no study has been performed with respect to a composite preparation of mosapride and rabeprazole.

DISCLOSURE

Technical Problem

An object of the present invention is to provide various forms of composite preparations which contain mosapride or a pharmaceutically acceptable salt thereof and rabeprazole or a pharmaceutically acceptable salt thereof.

Technical Solution

To achieve the above object, the present invention provides a composite preparation which has a core tablet structure in which a composition containing rabeprazole or a pharmaceutically acceptable salt thereof is contained as an inner core, and the outer layer of the composition is surrounded by a composition containing mosapride or a pharmaceutically acceptable salt thereof.

Additionally, the present invention provides a composite preparation in the form of a capsule in which a composition containing rabeprazole or a pharmaceutically acceptable salt thereof in the form of an enteric-coated tablet and a composition containing mosapride or a pharmaceutically acceptable salt thereof in the form of a multi-layer tablet are encapsulated.

Additionally, the present invention provides a composite preparation in the form of a capsule in which a composition containing rabeprazole or a pharmaceutically acceptable salt thereof in the form of an enteric-coated tablet and a composition containing mosapride or a pharmaceutically acceptable salt thereof containing at least one tablet are encapsulated.

Additionally, the present invention provides a composite preparation in the form of a capsule in which a composition containing rabeprazole or a pharmaceutically acceptable salt thereof in the form of an enteric-coated pellet and a composition containing mosapride or a pharmaceutically acceptable salt thereof containing at least one tablet are encapsulated.

Advantageous Effects of the Invention

The composite preparation prepared according to the present invention allows rapid release of a drug without deteriorating its release by an interaction between mosapride and rabeprazole, thus exhibiting an improved drug release rate and bioavailability, while having excellent product stability and being capable of significantly lowering the amount of the excipient. Accordingly, the composite preparation of the present invention can improve patients' drug compliance due to the size of its dosage form.

BEST MODE

Figure 1:
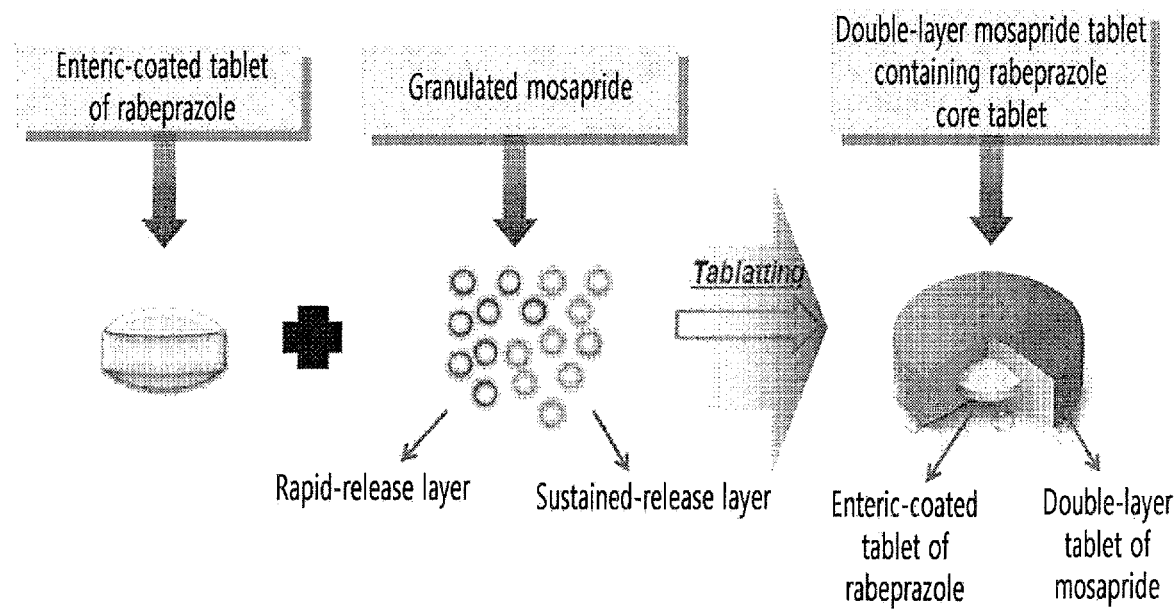
FIG. 1 shows an embodiment of the formulation of a composite preparation according to the invention, and specifically, a schematic diagram which briefly illustrates a composite preparation of a sustained-release tablet of mosapride in which a rabeprazole core tablet is contained.

4-Amino-5-chloro-2-ethoxy-N-[4-(4-fluorobenzyl)-2-morpholinyl]methylbenzamide (mosapride), which is an ingredient contained in the composite preparation of the present invention, is a compound having the structure of Formula 1 below. Mosapride acts selectively on serotonin (5-HT) receptors on cholinergic neurons of the digestive tract, and promotes the release of acetylcholine at the nerve endings. Acetylcholine is a serotonin receptor agonist that promotes smooth muscle movement of the digestive tract and exerts strong gastrointestinal motility and gastric emptying activity, and it is known to be advantageous to prepare mosapride with a formulation design which can gradually release the active ingredient while controlling the drug release rate using a sustained-release base with short blood half-life. Accordingly, it is preferred that the sustained-release preparation including a composition, which contains mosapride or a pharmaceutically acceptable salt thereof, exhibit the property of continuously releasing its active ingredient for 24 hours. In the present invention, the pharmaceutically acceptable salt of mosapride may be mosapride citrate, or may exist in the form of a hydrate thereof. In the present specification, mosapride or a pharmaceutically acceptable salt thereof is sometimes designated as a first active ingredient.

[Formula 1]

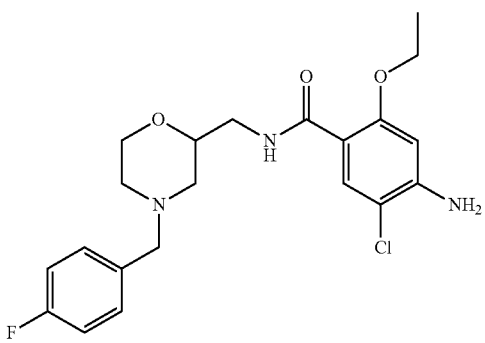

Additionally, rabeprazole, which is an ingredient of the composite preparation of the present invention, is a benzimidazole derivative that inhibits gastric acid secretion and has a structure of Formula 2. Rabeprazole is known as a proton pump inhibitor (PPI) that inhibits $H^+/K^+$ ATPase and inhibits gastric acid secretion on the surface of the parietal cells of the gastric mucosa for acid secretion. Furthermore, rabeprazole induces inhibition of basal acid secretion and acid secretion by stimulation and is thus attracting attention as a therapeutic agent for peptic ulcer, duodenal ulcer, etc. In the present invention, a pharmaceutically acceptable salt of rabeprazole may be a rabeprazole sodium salt, but is not limited thereto. In the present specification, rabeprazole or a pharmaceutically acceptable salt thereof is sometimes designated as a second active ingredient.

[Formula 2]

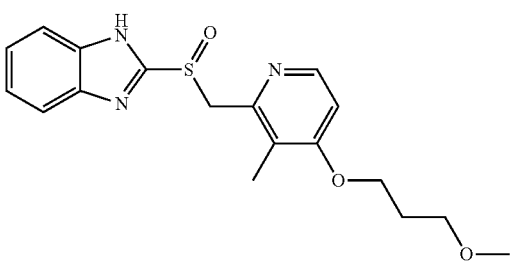

The composite preparation of the present invention can reduce the burden of patients with functional digestive disorders, who have been treated with mosapride, for additional administration of rabeprazole, a therapeutic agent for peptic ulcer, allowing rapid release of drugs without decrease of dissolution caused by the interaction of mosapride and rabeprazole. As a result, not only can the composite preparation of the present invention exhibit improved dissolution and bioavailability of the drug, but it also has excellent product stability and can significantly reduce the amounts of additives, thereby improving drug compliance of patients due to formulation size.

An aspect of the present invention provides a composite preparation having a core tablet structure, in which a rabeprazole composition (a second composition) is contained as an inner core and a mosapride composition (a first composition) surrounds the outer layer of the rabeprazole composition.

As shown in FIG. 1, the rabeprazole composition may be in the form of an enteric-coated tablet and the mosapride composition may be in the form of granules, but the forms of these compositions are not limited thereto. Additionally, as described above, it is advantageous that the mosapride composition be eluted slowly due to its short blood half-life, and thus the mosapride composition may contain not only granules with a rapid-release form as shown in FIG. 1, but also granules with a suspended-release form that contains a release-controlling agent.

The first active ingredient, which is mosapride or a pharmaceutically acceptable salt thereof, may be contained in an amount of 0.1 parts by weight to 10 parts by weight, and more specifically 1 part by weight to 5 parts by weight, based on 100 parts by weight of the total composite preparation, but the amount is not limited thereto.

Additionally, the first active ingredient may be contained in an amount of 1 part by weight to 20 parts by weight, and more specifically 3 parts by weight to 15 parts by weight, based on 150 parts by weight of the first composition. If the first composition is a rapid-release composition, the first active ingredient may be contained in an amount of 3 parts by weight to 7 parts by weight, based on 150 parts by weight of the first composition. If the first composition is a suspended-release composition, the first active ingredient may be contained in an amount of 8 parts by weight to 13 parts by weight, based on 150 parts by weight of the first composition.

According to an embodiment of the present invention, the mosapride composition in the form of granules may include a form such as a rapid-release layer (a rapid-release composition) containing an excipient, disintegrant, binder, glidant, etc. in addition to the first active ingredient; or a form of a suspended-release layer (a suspended-release composition) containing an excipient, disintegrant, release-controlling agent, binder, glidant, etc. in addition to the first active ingredient; or include both forms.

Non-limiting examples of the excipient for use in the composite preparation of the present invention may each independently be lactose, mannitol, glucose, sorbitol, dextrin, sucrose, or a mixture thereof. Lactose has the roles of improving the ease of tableting, facilitating the formation of water-soluble channels when coexisting with HPMC in an eluate, and retaining the form of tablets. Additionally, lactose is mixed with high-viscosity HPMC to enable homogeneous mixing with mosapride salts (e.g., mosapride citrate) and HPMC. The excipient may be contained in the first composition in an amount of 20 parts by weight to 40 parts by weight, and specifically 25 parts by weight to 35 parts by weight, based on 100 parts by weight of the total composite preparation. Additionally, the excipient may be contained in an amount of 30 parts by weight to 100 parts by weight, and more specifically 50 parts by weight to 90 parts by weight, based on 150 parts by weight of the first composition. If the first composition is a rapid-release composition, the excipient may be contained in an amount of 80 parts by weight to 90 parts by weight based on 150 parts by weight of the first composition. If the first composition is a suspended-release composition, the excipient may be contained in an amount of 50 parts by weight to 60 parts by weight based on 150 parts by weight of the first composition.

The disintegrant for use in the composite preparation of the present invention is used to enhance the dissolution of mosapride or rabeprazole and their salts by absorbing water to promote disintegration of the preparation. Non-limiting examples of the disintegrant for use in the present invention may each independently be croscarmellose sodium, sodium starch glycolate, microcrystalline cellulose, cross-linked povidone (crospovidone) and other commercially-available polyvinylpyrrolidone (PVP, povidone), low-substituted HPC, alginic acid, powdered cellulose, starch, sodium alginate, and a mixture thereof. Among these, low-substituted HPC and crospovidone are preferable. The disintegrant may be added in addition to the solid preparation for oral administration in a pharmaceutically acceptable manner and an additional second disintegrant may be used for the purpose of more rapid release of the preparation. The disintegrant in the first composition may be contained in an amount of 10 parts by weight to 30 parts by weight, and specifically 15 parts by weight to 25 parts by weight, based on 100 parts by weight of the total composite preparation. Additionally, the disintegrant may be contained in an amount of 20 parts by weight to 60 parts by weight, and more specifically 25 parts by weight to 50 parts by weight, based on 150 parts by weight of the first composition. If the first composition is a rapid-release composition, the disintegrant may be contained in an amount of 45 parts by weight to 50 parts by weight based on 150 parts by weight of the first composition. If the first composition is a suspended-release composition, the disintegrant may be contained in an amount of 25 parts by weight to 30 parts by weight based on 150 parts by weight of the first composition.

A binder which is soluble in an organic solvent as a water-soluble polymer and serves to increase the binding force of preparations can be used in the composite preparation of the present invention. Non-limiting examples of the binder to be used include polyvinylpyrrolidone (commonly known as povidone; povidone K-30 having a molecular weight of 30 is used), microcrystalline cellulose, methyl cellulose, calcium hydrogen phosphate, spray dried lactose, gelatin, etc. The binder may be contained in the first composition in an amount of 1 part by weight to 10 parts by weight, and more specifically 3 parts by weight to 7 parts by weight, based on 100 parts by weight of the total composite preparation. Additionally, the binder may be contained in an amount of 5 parts by weight to 15 parts by weight, and more specifically 7 parts by weight to 13 parts by weight, based on 150 parts by weight of the first composition.

Non-limiting examples of the glidant to be used for the composite preparation of the present invention may each be independently light anhydrous silicic acid, silicon dioxide, talc, stearic acid, magnesium stearate, or a mixture thereof. A glidant improves the fluidity of the particulate materials to increase the filling property into a die, which is a lower part of the tableting machine, and thereby reduces the friction between the particulate materials and between the particulate materials and the punch die, which is an upper part of the tableting machine, so as to facilitate compression and release of tablets. The glidant may be contained in the first composition in an amount of 0.1 parts by weight to 5 parts by weight, and specifically, 0.5 parts by weight to 2.5 parts by weight, based on 100 parts by weight of the total composite preparation. Additionally, the glidant may be contained in an amount of 0.5 parts by weight to 5 parts by weight, and more specifically 1 part by weight to 3 parts by weight, based on 150 parts by weight of the first composition.

The sustained-release agent (release-controlling agent) contained in the sustained-release layer of the mosapride composition may be used by mixing high-viscosity HPMC and low-viscosity HPMC. The release-controlling agent may be contained in an amount of 1 part by weight to 20 parts by weight, and specifically 5 parts by weight to 15 parts by weight, based on 100 parts by weight of the total composite preparation. Additionally, the release-controlling agent may be contained in an amount of 30 parts by weight to 60 parts by weight, and more specifically 40 parts by weight to 50 parts by weight, based on 150 parts by weight of the first composition for suspended release.

Waxes may be used instead of the high-viscosity HPMC used in the first composition for suspended release, and a similar dissolution profile may be exhibited as a result. That is, the release-controlling agent for suspended release may be prepared by mixing low-viscosity HPMC with waxes instead of high-viscosity HPMC. In particular, waxes and low-viscosity HPMC may be mixed in a weight ratio of 20:1 to 5:1. Non-limiting examples of the waxes to be used include microcrystalline wax, anionic wax, anionic emulsified wax, bleached wax, carnauba wax, cetyl ester wax, beeswax, caster wax, cationic emulsified wax, cetrimide emulsified wax, emulsified wax, glyceryl behenate, nonionic wax, nonionic emulsified wax, paraffin, petroleum wax, scale wax, white wax, yellow wax, mixtures thereof, etc. Preferably, the wax can exhibit effectiveness when microcrystalline wax, carnauba wax, glyceryl behenate, etc. are used as the wax. The waxes may preferably be used in an amount of 20 parts by weight to 32 parts by weight, and more preferably, 24 parts by weight to 31 parts by weight, based on 100 parts by weight of the total composite preparation, but the amount is not limited thereto.

Additionally, the release-controlling agent constituting the suspended-release layer may be used by mixing the high-viscosity HPMC having a viscosity of 80,000 cps to 120,000 cps and the low-viscosity HPMC having a viscosity of 2,000 cps to 20,000 cps at a weight ratio in the range of 2.5:1 to 1:1, whereby the composite preparation complies with the dissolution profile according to the second method of the dissolution test (paddle method) of the Korean Pharmacopoeia that the first active ingredient comprised in the water eluent at 37° C. and pH 4.0 is released in the range of 25% to 45% of the total weight of the first active ingredient in 1 hour, 60% to 80% of the total weight of the first active ingredient in 8 hours, and at least 85% of the total weight of the first active ingredient in 24 hours.

According to an embodiment of the present invention, the release-controlling agent may be used by mixing the high-viscosity HPMC and the low-viscosity HPMC at a weight ratio in the range of 1.2:1 to 1:1, whereby the composite preparation complies with the dissolution profile according to the second method of the dissolution test (paddle method) of the Korean Pharmacopoeia that the first active ingredient comprised in the water eluent at 37° C. and pH 4.0 is released in the range of 40% to 45% of the total weight of the first active ingredient in 1 hour, 70% to 75% of the total weight of the first active ingredient in 8 hours, and at least 90% of the total weight of the first active ingredient in 24 hours.

Additionally, according to an embodiment of the present invention, the rabeprazole composition in the form of an enteric-coated tablet may contain an excipient, alkalizing agent, disintegrant, binder, or glidant. In particular, the excipient, disintegrant, binder, and glidan are the same as explained above.

A second active ingredient, which is rabeprazole or a pharmaceutically acceptable salt thereof, may be contained in an amount of 0.1 parts by weight to 10 parts by weight, and more specifically 1 part by weight to 5 parts by weight, based on 100 parts by weight of the total composite preparation, but the amount is not limited thereto. Additionally, the second active ingredient may be contained in an amount of 1 part by weight to 20 parts by weight, and more specifically 5 parts by weight to 15 parts by weight, based on 130 parts by weight of the second composition.

The excipient may be contained in the second composition in an amount of 1 part by weight to 20 parts by weight, and specifically 5 parts by weight to 15 parts by weight, based on 100 parts by weight of the total composite preparation. Additionally, the excipient may be contained in an amount of 30 parts by weight to 60 parts by weight, and more specifically 40 parts by weight to 50 parts by weight, based on 130 parts by weight of the second composition.

The disintegrant may be contained in the second composition in an amount of 0.5 parts by weight to 15 parts by weight, and specifically 1 part by weight to 7 parts by weight, based on 100 parts by weight of the total composite preparation. Additionally, the disintegrant may be contained in an amount of 5 parts by weight to 20 parts by weight, and more specifically 10 parts by weight to 15 parts by weight, based on 130 parts by weight of the second composition.

The binder may be contained in the second composition in an amount of 0.1 parts by weight to 5 parts by weight, and specifically 0.5 parts by weight to 2.5 parts by weight, based on 100 parts by weight of the total composite preparation. Additionally, the binder may be contained in an amount of 0.5 parts by weight to 10 parts by weight, and more specifically 1 part by weight to 5 parts by weight, based on 130 parts by weight of the second composition.

The glidant may be contained in the second composition in an amount of 0.1 parts by weight to 5 parts by weight, and specifically 0.5 parts by weight to 2.5 parts by weight, based on 100 parts by weight of the total composite preparation. Additionally, the glidant may be contained in an amount of 0.5 parts by weight to 10 parts by weight, and more specifically 1 part by weight to 5 parts by weight, based on 130 parts by weight of the second composition.

When a second composition containing rabeprazole or a salt thereof is used as an enteric-coated tablet, an alkalifying agent may be contained therein. The alkalifying agent may be contained in the second composition in an amount of 1 part by weight to 20 parts by weight, and specifically 5 parts by weight to 15 parts by weight, based on 100 parts by weight of the total composite preparation. Additionally, the alkalifying agent may be contained in an amount of 30 parts by weight to 60 parts by weight, and more specifically 40 parts by weight to 50 parts by weight, based on 130 parts by weight of the second composition. Examples of the alkalifying agent to be used may include magnesium oxide, calcium carbonate, dicalcium phosphate, tricalcium phosphate, magnesium carbonate, magnesium hydroxide, magnesium silicate, magnesium aluminate, magnesium aluminum hydroxide, potassium hydroxide, sodium bicarbonate, sodium carbonate, sodium hydroxide, etc., and specifically, magnesium oxide and calcium hydroxide, but the alkalifying agent is not limited thereto.

The second composition containing rabeprazole or a salt thereof may be in the form of an enteric-coated tablet that remains intact without being dissolved in the stomach by gastric acid and is released when the composition is moved down to the small intestine, and may contain an enteric-coating agent for its preparation. The enteric-coating agent may be contained in the second composition in an amount of 0.1 parts by weight to 10 parts by weight, and specifically 1 part by weight to 5 parts by weight, based on 100 parts by weight of the total composite preparation. Additionally, the enteric-coating agent may be contained in an amount of 1 part by weight to 20 parts by weight, and more specifically 5 parts by weight to 15 parts by weight, based on 130 parts by weight of the second composition.

Additionally, a composite preparation in a core tablet formulation may be completed by finally coating the first and second compositions using a coating agent. For the coating agent, HPMC or Opadry-OY-C-7000A may be used, but the coating agent is not limited thereto. The coating agent may be contained in an amount of 0.1 parts by weight to 5 parts by weight, and specifically 0.5 parts by weight to 2.5 parts by weight, based on 100 parts by weight of the total composite preparation.

According to an embodiment of the present invention, the composite preparation of the present invention may be prepared according to the method for preparing a composite preparation including:

i) preparing an enteric-coated tablet containing rabeprazole or a pharmaceutically acceptable salt thereof, excipient, and alkalifying agent;

ii) preparing a granulated product for rapid release containing mosapride or a pharmaceutically acceptable salt thereof;

iii) preparing a granulated product for suspended release containing mosapride or a pharmaceutically acceptable salt thereof and a release-controlling agent;

iv) tableting into a core tablet, in which the enteric-coated tablet prepared in i) is contained as an inner core; and a granulated product for suspended release and a granulated product for suspended release prepared in steps ii) and iii) are contained as an outer layer; and v) coating the core tablet.

In the above preparation method, the products of steps i) to iii) may be prepared in any order and these products may be produced simultaneously.

Another aspect of the present invention provides a composite preparation in the form of a capsule, which contains a rabeprazole composition (a second composition) in the form of an enteric-coated tablet and a mosapride composition (a first composition) in the form of a multi-layer tablet.

Figure 2:
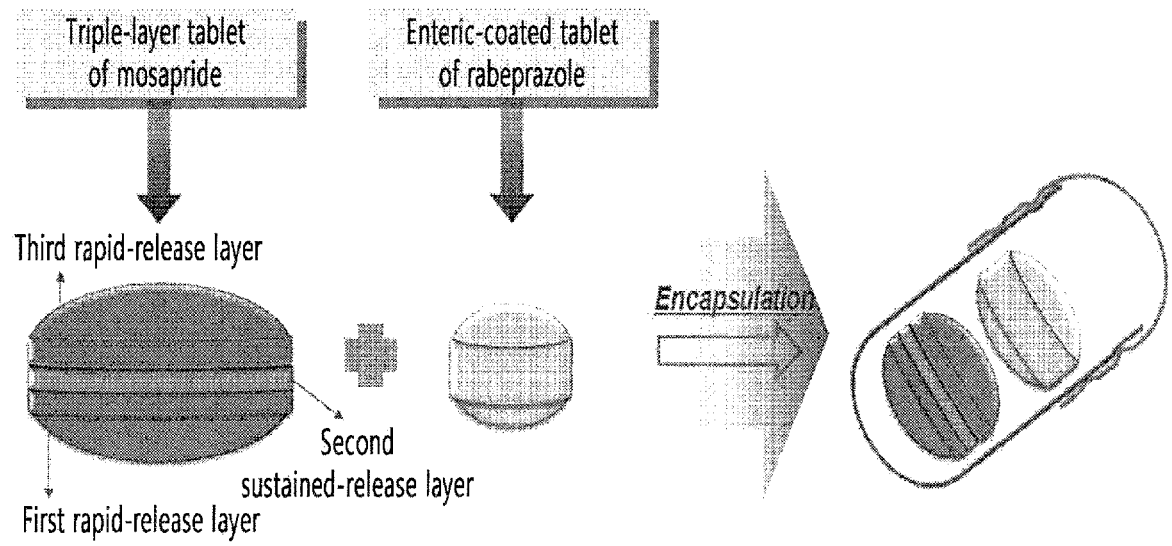
FIG. 2 shows an embodiment of the formulation of a composite preparation according to the invention, and specifically, a schematic diagram which briefly illustrates a composite preparation in which a rabeprazole tablet and a triple-layer tablet of mosapride are encapsulated in a capsule.

As shown in FIG. 2, the rabeprazole composition may be prepared in the form of an enteric-coated tablet and the mosapride composition may be prepared in the form of a multi-layer tablet. The present invention provides a composite preparation in the form of a capsule including each of these compositions.

Additionally, as described above, it is preferred that the mosapride composition be released slowly due to its short blood half-life. The mosapride composition may be prepared in the form of a multi-layer tablet where a sustained-release layer is inserted between rapid-release layers, as shown in FIG. 2.

The first active ingredient (i.e., mosapride or a pharmaceutically acceptable salt thereof) may be contained in an amount of 0.1 parts by weight to 10 parts by weight, and more specifically 2 parts by weight to 7 parts by weight, based on 100 parts by weight of the total composite preparation, but the amount is not limited thereto.

Additionally, the first active ingredient may be contained in an amount of 1 part by weight to 20 parts by weight, and more specifically 2 parts by weight to 15 parts by weight, based on 75 parts by weight of the first composition. If the first composition is a rapid-release composition, the first active ingredient may be contained in an amount of 2 parts by weight to 5 parts by weight, based on 75 parts by weight of the first composition. If the first composition is a suspended-release composition, the first active ingredient may be contained in an amount of 8 parts by weight to 13 parts by weight, based on 75 parts by weight of the first composition.

According to an embodiment of the present invention, the mosapride composition in the form of a multi-layer tablet may include a rapid-release layer which contains an excipient, disintegrant, binder, glidant, etc. in addition to the first active ingredient; or a suspended-release layer which contains an excipient, disintegrant, release-controlling agent, binder, glidant, etc. in addition to the first active ingredient, and the mosapride composition may be prepared in a triple-layer form in which a suspended-release layer is inserted between rapid-release layers as shown in FIG. 2, but its form is not limited thereto. Meanwhile, the mosapride composition may be prepared in the form where a rapid-release layer is inserted between suspended-release layers. Here, the excipient, disintegrant, binder, glidant, and release-controlling agent are the same as explained above.

The excipient may be contained in the first composition in an amount of 20 parts by weight to 40 parts by weight, and specifically 25 parts by weight to 35 parts by weight, based on 100 parts by weight of the total composite preparation. Additionally, the excipient may be contained in an amount of 15 parts by weight to 50 parts by weight, and more specifically 20 parts by weight to 45 parts by weight, based on 75 parts by weight of the first composition. If the first composition is a rapid-release composition, the excipient may be contained in an amount of 30 parts by weight to 45 parts by weight, based on 75 parts by weight of the first composition. If the first composition is a suspended-release composition, the excipient may be contained in an amount of 20 parts by weight to 30 parts by weight, based on 75 parts by weight of the first composition.

The disintegrant may be contained in the first composition in an amount of 10 parts by weight to 30 parts by weight, and specifically 15 parts by weight to 25 parts by weight, based on 100 parts by weight of the total composite preparation. Additionally, the disintegrant may be contained in an amount of 5 parts by weight to 35 parts by weight, and more specifically 10 parts by weight to 30 parts by weight, based on 75 parts by weight of the first composition. If the first composition is a rapid-release composition, the disintegrant may be contained in an amount of 20 parts by weight to 30 parts by weight, based on 75 parts by weight of the first composition. If the first composition is a suspended-release composition, the disintegrant may be contained in an amount of 10 parts by weight to 20 parts by weight, based on 75 parts by weight of the first composition.

The binder may be contained in the first composition in an amount of 1 part by weight to 10 parts by weight, and specifically 2 parts by weight to 7 parts by weight, based on 100 parts by weight of the total composite preparation. Additionally, the binder may be contained in an amount of 0.5 parts by weight to 10 parts by weight, and more specifically 1 part by weight to 7 parts by weight, based on 75 parts by weight of the first composition.

The glidant may be contained in the first composition in an amount of 0.05 parts by weight to 5 parts by weight, and specifically 0.1 parts by weight to 2.5 parts by weight, based on 100 parts by weight of the total composite preparation. Additionally, the glidant may be contained in an amount of 0.1 parts by weight to 5 parts by weight, and more specifically 0.5 parts by weight to 2 parts by weight, based on 75 parts by weight of the first composition.

The sustained-release agent (release-controlling agent) contained in the sustained-release layer of the mosapride composition may be used by mixing high-viscosity HPMC and low-viscosity HPMC. The release-controlling agent may be contained in an amount of 1 part by weight to 20 parts by weight, and specifically 3 parts by weight to 10 parts by weight, based on 100 parts by weight of the total composite preparation. Additionally, the release-controlling agent may be contained in an amount of 10 parts by weight to 40 parts by weight, and more specifically 20 parts by weight to 30 parts by weight, based on 75 parts by weight of the first composition for suspended release.

Additionally, the release-controlling agent constituting the suspended-release layer may be used by mixing the high-viscosity HPMC having a viscosity of 80,000 cps to 120,000 cps and the low-viscosity HPMC having a viscosity of 2,000 cps to 20,000 cps at a weight ratio in the range of 2.5:1 to 1:1, and preferably 1.75:1 to 1:1, whereby the composite preparation complies with the dissolution profile according to the second method of the dissolution test (paddle method) of the Korean Pharmacopoeia that the first active ingredient comprised in the water eluent at 37° C. and pH 4.0 is released in the range of 25% to 45% of the total weight of the first active ingredient in 1 hour, 60% to 80% of the total weight of the first active ingredient in 8 hours, and at least 85% of the total weight of the first active ingredient in 24 hours.

Additionally, according to an embodiment of the present invention, the rabeprazole composition in the form of an enteric-coated tablet may contain an excipient, alkalifying agent, disintegrant, binder, glidant, etc. in addition to the second active ingredient. In particular, the excipient, disintegrant, binder, and glidant are the same as explained above.

The second active ingredient (i.e., rabeprazole or a pharmaceutically acceptable salt thereof) may be contained in an amount of 0.1 parts by weight to 10 parts by weight, and more specifically 1 part by weight to 5 parts by weight, based on 100 parts by weight of the total composite preparation, but the amount is not limited thereto. Additionally, the second active ingredient may be contained in an amount of 1 part by weight to 20 parts by weight, and more specifically 5 parts by weight to 15 parts by weight, based on 130 parts by weight of the second composition.

The excipient may be contained in the second active ingredient in an amount of 1 part by weight to 20 parts by weight, and specifically 5 parts by weight to 15 parts by weight, based on 100 parts by weight of the total composite preparation. Additionally, the excipient may be contained in an amount of 30 parts by weight to 60 parts by weight, and more specifically 35 parts by weight to 50 parts by weight, based on 130 parts by weight of the second composition.

The disintegrant may be contained in the second active ingredient in an amount of 0.5 parts by weight to 15 parts by weight, and specifically 1 part by weight to 7 parts by weight, based on 100 parts by weight of the total composite preparation. Additionally, the disintegrant may be contained in an amount of 5 parts by weight to 30 parts by weight, and more specifically 10 parts by weight to 20 parts by weight, based on 130 parts by weight of the second composition.

The binder may be contained in the second active ingredient in an amount of 0.1 parts by weight to 5 parts by weight, and specifically 0.5 parts by weight to 2.5 parts by weight, based on 100 parts by weight of the total composite preparation. Additionally, the binder may be contained in an amount of 0.5 parts by weight to 10 parts by weight, and more specifically 1 part by weight to 5 parts by weight, based on 130 parts by weight of the second composition.

The glidant may be contained in the second active ingredient in an amount of 0.1 parts by weight to 5 parts by weight, and specifically 0.5 parts by weight to 2.5 parts by weight, based on 100 parts by weight of the total composite preparation. Additionally, the glidant may be contained in an amount of 0.5 parts by weight to 10 parts by weight, and more specifically 1 part by weight to 5 parts by weight, based on 130 parts by weight of the second composition.

When the second composition containing rabeprazole or a salt thereof is used as an enteric-coated tablet, an alkalifying agent such as magnesium oxide may be contained therein. The alkalifying agent may be contained in the second composition in an amount of 1 part by weight to 20 parts by weight, and specifically 5 parts by weight to 15 parts by weight, based on 100 parts by weight of the total composite preparation. Additionally, the alkalifying agent may be contained in an amount of 30 parts by weight to 60 parts by weight, and more specifically 35 parts by weight to 50 parts by weight, based on 130 parts by weight of the second composition.

The second composition containing rabeprazole or a salt thereof may be in the form of an enteric-coated tablet that remains intact without being dissolved in the stomach by gastric acid and is released when the composition is moved down to the small intestine, and may contain an enteric-coating agent for its preparation. The enteric-coating agent may be contained in the second composition in an amount of 0.1 parts by weight to 10 parts by weight, and specifically 1 part by weight to 5 parts by weight, based on 100 parts by weight of the total composite preparation. Additionally, the enteric-coating agent may be contained in an amount of 1 part by weight to 20 parts by weight, and more specifically 5 parts by weight to 15 parts by weight, based on 130 parts by weight of the second composition.

Additionally, the capsule used in the composite preparation of the present invention may be a hard capsule or soft capsule. The base of the capsules may be selected from the group consisting of hypromellose, pullulan, gelatin, polyvinyl alcohol, and mixtures thereof, but the base is not limited thereto, and any material which can be conventionally used for the capsule film may be used.

According to an embodiment of the present invention, the composite preparation of the present invention may be prepared according to the method for preparing a composite preparation including:

i) preparing an enteric-coated tablet containing rabeprazole or a pharmaceutically acceptable salt thereof, excipient, and alkalifying agent;

ii) preparing a granulated product for rapid release containing mosapride or a pharmaceutically acceptable salt thereof;

iii) preparing a granulated product for suspended release containing mosapride or a pharmaceutically acceptable salt thereof and a release-controlling agent;

iv) preparing a mosapride-containing multi-layer tablet for rapid release by tableting the granulated product for rapid release and the granulated product for suspended release; and v) filling the mosapride-containing multi-layer tablet and the rabeprazole-containing enteric-coated tablet into a hard capsule.

In the above preparation method, the products of steps i) to iii) may be prepared in any order and these products may be produced simultaneously, and the mosapride-containing multi-layer tablet may have a final hardness of 10 MPa to 14 MPa.

Still another aspect of the present invention provides a composite preparation in the form of a capsule, which includes a rabeprazole composition (a second composition) in the form of an enteric-coated tablet and a mosapride composition (a first composition) containing at least one tablet.

Figure 3:
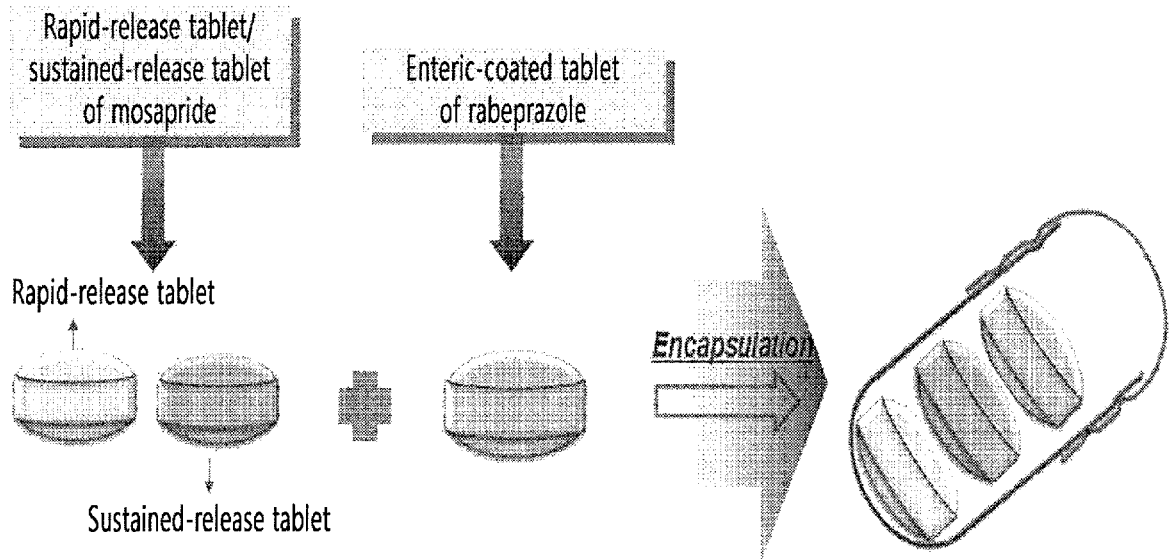
FIG. 3 shows an embodiment of the formulation of a composite preparation according to the invention, and specifically, a schematic diagram which briefly illustrates a composite preparation in which a rapid-release tablet/sustained-release tablet of mosapride and an enteric-coated tablet of rabeprazole are encapsulated in a capsule.

As shown in FIG. 3, the rabeprazole composition may be in the form of an enteric-coated tablet and the mosapride composition may be in the form of at least one tablet, and preferably two tablets of one rapid-release tablet and one suspended-release tablet, but the forms of these compositions are not limited thereto. The preparation of the present invention may be in the form of a capsule including each of these compositions.

The first active ingredient (i.e., mosapride or a pharmaceutically acceptable salt thereof) may be contained in an amount of 0.1 parts by weight to 15 parts by weight, and more specifically 3 parts by weight to 10 parts by weight, based on 100 parts by weight of the total composite preparation, but the amount is not limited thereto.

Additionally, the first active ingredient may be contained in an amount of 1 part by weight to 20 parts by weight, and more specifically 2 parts by weight to 15 parts by weight, based on 75 parts by weight of the first composition. If the first composition is a rapid-release composition, the first active ingredient may be contained in an amount of 3 parts by weight to 7 parts by weight, based on 150 parts by weight of the first composition. If the first composition is a suspended-release composition, the first active ingredient may be contained in an amount of 8 parts by weight to 13 parts by weight, based on 150 parts by weight of the first composition.

According to an embodiment of the present invention, the mosapride composition may include at least one rapid-release tablet containing an excipient, disintegrant, binder, glidant, etc. in addition to the first active ingredient; or at least one suspended-release tablet containing an excipient, disintegrant, release-controlling agent, binder, glidant, etc. in addition to the first active ingredient; or include both forms, and the mosapride composition may be used as a composite preparation in the form of a capsule in which the suspended-release tablet(s), the rapid-release tablet(s), and a rabeprazole composition in the form of an enteric-coated tablet are encapsulated together into a capsule. In particular, the excipient, disintegrant, binder, glidant, release-controlling agent, and capsule agent are the same as explained above.

The excipient may be contained in the first composition in an amount of 10 parts by weight to 40 parts by weight, and specifically 20 parts by weight to 30 parts by weight, based on 100 parts by weight of the total composite preparation. Additionally, the excipient may be contained in an amount of 15 parts by weight to 50 parts by weight, and more specifically 20 parts by weight to 45 parts by weight, based on 75 parts by weight of the first composition. If the first composition is a rapid-release composition, the excipient may be contained in an amount of 30 parts by weight to 45 parts by weight, based on 75 parts by weight of the first composition. If the first composition is a suspended-release composition, the excipient may be contained in an amount of 20 parts by weight to 30 parts by weight, based on 75 parts by weight of the first composition.

The disintegrant may be contained in the first composition in an amount of 5 parts by weight to 30 parts by weight, and specifically 10 parts by weight to 20 parts by weight, based on 100 parts by weight of the total composite preparation. Additionally, the disintegrant may be contained in an amount of 5 parts by weight to 35 parts by weight, and more specifically 10 parts by weight to 30 parts by weight, based on 75 parts by weight of the first composition. If the first composition is a rapid-release composition, the disintegrant may be contained in an amount of 20 parts by weight to 30 parts by weight, based on 75 parts by weight of the first composition. If the first composition is a suspended-release composition, the disintegrant may be contained in an amount of 10 parts by weight to 20 parts by weight, based on 75 parts by weight of the first composition.

The binder may be contained in the first composition in an amount of 1 part by weight to 10 parts by weight, and specifically 3 parts by weight to 7 parts by weight, based on 100 parts by weight of the total composite preparation. Additionally, the binder may be contained in an amount of 0.5 parts by weight to 10 parts by weight, and more specifically 1 part by weight to 7 parts by weight, based on 75 parts by weight of the first composition.

The glidant may be contained in the composition in an amount of 0.1 parts by weight to 5 parts by weight, and specifically 0.5 parts by weight to 2.5 parts by weight, based on 100 parts by weight of the total composite preparation. Additionally, the glidant may be contained in an amount of 0.1 parts by weight to 5 parts by weight, and more specifically 0.5 parts by weight to 3 parts by weight, based on 75 parts by weight of the first composition.

The sustained-release agent (release-controlling agent) contained in the sustained-release layer of the mosapride composition may be used by mixing high-viscosity HPMC and low-viscosity HPMC. The release-controlling agent may be contained in an amount of 1 part by weight to 20 parts by weight, and specifically 5 parts by weight to 15 parts by weight, based on 100 parts by weight of the total composite preparation. Additionally, the release-controlling agent may be contained in an amount of 10 parts by weight to 40 parts by weight, and more specifically 20 parts by weight to 30 parts by weight, based on 75 parts by weight of the first composition for suspended release.

Additionally, the release-controlling agent constituting the suspended-release layer may be used by mixing the high-viscosity HPMC having a viscosity of 80,000 cps to 120,000 cps and the low-viscosity HPMC having a viscosity of 2,000 cps to 20,000 cps at a weight ratio in the range of 2.5:1 to 1:1, and preferably 1.75:1 to 1:1, whereby the composite preparation complies with the dissolution profile according to the second method of the dissolution test (paddle method) of the Korean Pharmacopoeia that the first active ingredient comprised in the water eluent at 37° C. and pH 4.0 is released in the range of 25% to 45% of the total weight of the first active ingredient in 1 hour, 60% to 80% of the total weight of the first active ingredient in 8 hours, and at least 85% of the total weight of the first active ingredient in 24 hours.

Additionally, according to an embodiment of the present invention, the rabeprazole composition in the form of an enteric-coated tablet may contain an excipient, alkalifying agent, disintegrant, binder, glidant, etc. in addition to the second active ingredient. In particular, the excipient, disintegrant, binder, and glidant are the same as explained above.

The second active ingredient (i.e., rabeprazole or a pharmaceutically acceptable salt thereof) may be contained in an amount of 0.1 parts by weight to 10 parts by weight, and more specifically 1 part by weight to 5 parts by weight, based on 100 parts by weight of the total composite preparation, but the amount is not limited thereto. Additionally, the second active ingredient may be contained in an amount of 1 part by weight to 20 parts by weight, and more specifically 5 parts by weight to 15 parts by weight, based on 130 parts by weight of the second composition.

The excipient may be contained in the second active ingredient in an amount of 5 parts by weight to 30 parts by weight, and specifically 10 parts by weight to 20 parts by weight, based on 100 parts by weight of the total composite preparation. Additionally, the excipient may be contained in an amount of 30 parts by weight to 60 parts by weight, and more specifically 35 parts by weight to 50 parts by weight, based on 130 parts by weight of the second composition.

The disintegrant may be contained in the second active ingredient in an amount of 0.5 parts by weight to 15 parts by weight, and specifically 1 part by weight to 7 parts by weight, based on 100 parts by weight of the total composite preparation. Additionally, the disintegrant may be contained in an amount of 5 parts by weight to 30 parts by weight, and more specifically 10 parts by weight to 20 parts by weight, based on 130 parts by weight of the second composition.

The binder may be contained in the second active ingredient in an amount of 0.1 parts by weight to 5 parts by weight, and specifically 0.5 parts by weight to 2.5 parts by weight, based on 100 parts by weight of the total composite preparation. Additionally, the binder may be contained in an amount of 0.5 parts by weight to 10 parts by weight, and more specifically 1 part by weight to 5 parts by weight, based on 130 parts by weight of the second composition.

The glidant may be contained in the second active ingredient in an amount of 0.1 parts by weight to 5 parts by weight, and specifically 0.5 parts by weight to 2.5 parts by weight, based on 100 parts by weight of the total composite preparation. Additionally, the glidant may be contained in an amount of 0.5 parts by weight to 10 parts by weight, and more specifically 1 part by weight to 5 parts by weight, based on 130 parts by weight of the second composition.

When the second composition containing rabeprazole or a salt thereof is used as an enteric-coated tablet, an alkalifying agent such as magnesium oxide may be contained therein. The alkalifying agent may be contained in the second composition in an amount of 1 part by weight to 30 parts by weight, and specifically 10 parts by weight to 20 parts by weight, based on 100 parts by weight of the total composite preparation. Additionally, the alkalifying agent may be contained in an amount of 30 parts by weight to 60 parts by weight, and more specifically 35 parts by weight to 50 parts by weight, based on 130 parts by weight of the second composition.

The second composition containing rabeprazole or a salt thereof may be in the form of an enteric-coated tablet that remains intact without being dissolved in the stomach by gastric acid and is released when the composition is moved down to the small intestine, and may contain an enteric-coating agent for its preparation. The enteric-coating agent may be contained in the second composition in an amount of 0.1 parts by weight to 10 parts by weight, and specifically 1 part by weight to 5 parts by weight, based on 100 parts by weight of the total composite preparation. Additionally, the enteric-coating agent may be contained in an amount of 1 part by weight to 20 parts by weight, and more specifically 5 parts by weight to 15 parts by weight, based on 130 parts by weight of the second composition.

According to an embodiment of the present invention, the composite preparation of the present invention may be prepared according to the method for preparing a composite preparation including:

i) preparing an enteric-coated tablet containing rabeprazole or a pharmaceutically acceptable salt thereof, excipient, and alkalifying agent;

ii) preparing a rapid-release tablet containing mosapride or a pharmaceutically acceptable salt thereof;

iii) preparing a suspended-release tablet containing mosapride or a pharmaceutically acceptable salt thereof and a release-controlling agent; and iv) filling the rapid-release tablet, suspended-release tablet, and enteric-coated tablet into a capsule.

In the above preparation method, the products of steps i) to iii) may be prepared in any order and these products may be produced simultaneously, and the rapid-release tablet and suspended-release tablet may have a final hardness of 10 MPa to 14 MPa.

Still another aspect of the present invention provides a composite preparation in the form of a capsule, which includes a rabeprazole composition (a second composition) in the form of an enteric-coated pellet and a mosapride composition (a first composition) containing at least one tablet.

Figure 4:
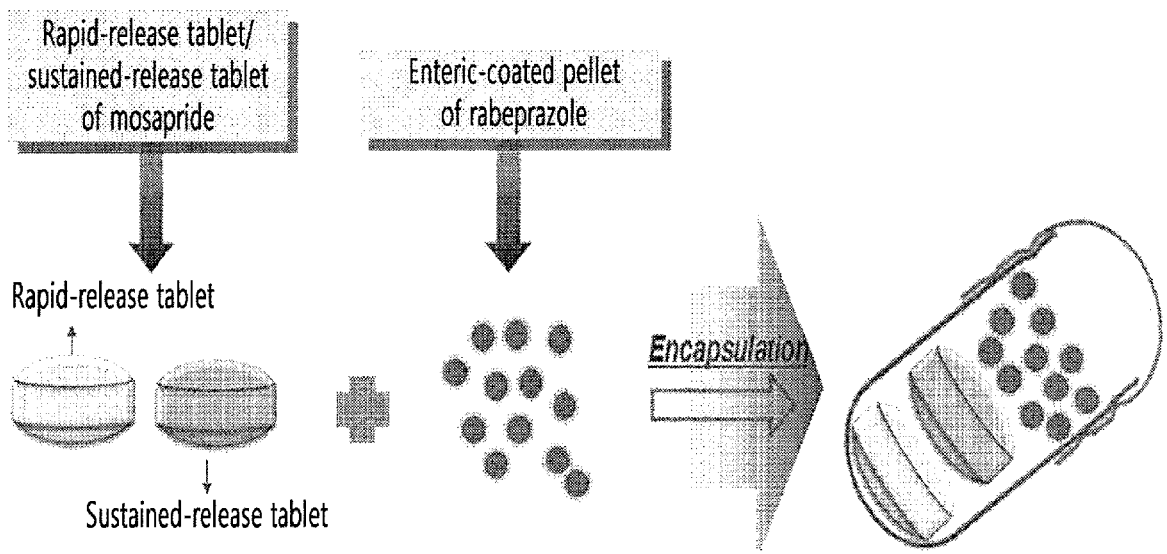
FIG. 4 shows an embodiment of the formulation of a composite preparation according to the invention, and specifically, a schematic diagram which briefly illustrates a composite preparation in which a rapid-release tablet/sustained-release tablet of mosapride and a pellet of rabeprazole are encapsulated in a capsule.

As shown in FIG. 4, the rabeprazole composition may be in the form of an enteric-coated pellet and the mosapride composition may be in the form of at least one tablet, and preferably two tablets of one rapid-release tablet and one suspended-release tablet, but the forms of these compositions are not limited thereto. The preparation of the present invention may be in the form of a capsule including each of these compositions.

The first active ingredient (i.e., mosapride or a pharmaceutically acceptable salt thereof) may be contained in an amount of 0.1 parts by weight to 15 parts by weight, and more specifically 3 parts by weight to 10 parts by weight, based on 100 parts by weight of the total composite preparation, but the amount is not limited thereto.

Additionally, the first active ingredient may be contained in an amount of 1 part by weight to 20 parts by weight, and more specifically 2 parts by weight to 15 parts by weight, based on 75 parts by weight of the first composition. If the first composition is a rapid-release composition, the first active ingredient may be contained in an amount of 2 parts by weight to 7 parts by weight, based on 75 parts by weight of the first composition. If the first composition is a suspended-release composition, the first active ingredient may be contained in an amount of 8 parts by weight to 13 parts by weight, based on 75 parts by weight of the first composition.

According to an embodiment of the present invention, the mosapride composition may include at least one rapid-release tablet containing an excipient, disintegrant, binder, glidant, etc. in addition to the first active ingredient; or at least one suspended-release tablet containing an excipient, disintegrant, release-controlling agent, binder, glidant, etc. in addition to the first active ingredient; or include both forms, and the mosapride composition may be used as a composite preparation in the form of a capsule in which the suspended-release tablet(s), the rapid-release tablet(s), and a rabeprazole composition in the form of an enteric-coated tablet are encapsulated together into a capsule. In particular, the excipient, disintegrant, binder, glidant, release-controlling agent, and capsule agent are the same as explained above.

The excipient may be contained in the first composition in an amount of 20 parts by weight to 40 parts by weight, and specifically 25 parts by weight to 35 parts by weight, based on 100 parts by weight of the total composite preparation. Additionally, the excipient may be contained in an amount of 15 parts by weight to 50 parts by weight, and more specifically 20 pans by weight to 45 parts by weight, based on 75 parts by weight of the first composition. If the first composition is a rapid-release composition, the excipient may be contained in an amount of 30 parts by weight to 45 parts by weight, based on 75 parts by weight of the first composition. If the first composition is a suspended-release composition, the excipient may be contained in an amount of 20 parts by weight to 30 parts by weight, based on 75 parts by weight of the first composition.

The disintegrant may be contained in the first composition in an amount of 10 parts by weight to 30 parts by weight, and specifically 15 parts by weight to 25 parts by weight, based on 100 parts by weight of the total composite preparation. Additionally, the disintegrant may be contained in an amount of 5 parts by weight to 35 parts by weight, and more specifically 10 parts by weight to 30 parts by weight, based on 75 parts by weight of the first composition. If the first composition is a rapid-release composition, the disintegrant may be contained in an amount of 20 parts by weight to 30 parts by weight, based on 75 parts by weight of the first composition. If the first composition is a suspended-release composition, the disintegrant may be contained in an amount of 10 parts by weight to 20 parts by weight, based on 75 parts by weight of the first composition.

The binder may be contained in the first composition in an amount of 1 part by weight to 10 parts by weight, and specifically 3 parts by weight to 7 parts by weight, based on 100 parts by weight of the total composite preparation. Additionally, the binder may be contained in an amount of 0.5 parts by weight to 10 parts by weight, and more specifically 1 part by weight to 7 parts by weight, based on 75 parts by weight of the first composition.

The glidant may be contained in the first composition in an amount of 0.1 parts by weight to 5 parts by weight, and specifically 0.5 parts by weight to 2.5 parts by weight, based on 100 parts by weight of the total composite preparation. Additionally, the glidant may be contained in an amount of 0.1 parts by weight to 5 parts by weight, and more specifically 0.5 parts by weight to 3 parts by weight, based on 75 parts by weight of the first composition.

The sustained-release agent (release-controlling agent) contained in the sustained-release layer of the mosapride composition may be used by mixing high-viscosity HPMC and low-viscosity HPMC. The release-controlling agent may be contained in an amount of 1 part by weight to 20 parts by weight, and specifically 5 parts by weight to 15 parts by weight, based on 100 parts by weight of the total composite preparation. Additionally, the release-controlling agent may be contained in an amount of 10 parts by weight to 40 parts by weight, and more specifically 20 parts by weight to 30 parts by weight, based on 75 parts by weight of the first composition for suspended release.

Additionally, the release-controlling agent constituting the suspended-release layer may be used by mixing the high-viscosity HPMC having a viscosity of 80,000 cps to 120,000 cps and the low-viscosity HPMC having a viscosity of 2,000 cps to 20,000 cps at a weight ratio in the range of 2.5:1 to 1:1, and preferably 1.75:1 to 1:1, whereby the composite preparation complies with the dissolution profile according to the second method of the dissolution test (paddle method) of the Korean Pharmacopoeia that the first active ingredient comprised in the water eluent at 37° C. and pH 4.0 is released in the range of 25% to 45% of the total weight of the first active ingredient in 1 hour, 60% to 80% of the total weight of the first active ingredient in 8 hours, and at least 85% of the total weight of the first active ingredient in 24 hours.

Additionally, according to an embodiment of the present invention, the rabeprazole composition in the form of an enteric-coated pellet may contain an excipient, coating agent, enteric-coating agent, etc. in addition to the second active ingredient. In particular, the excipient, coating agent, and enteric-coating agent are the same as explained above.

The second active ingredient (i.e., rabeprazole or a pharmaceutically acceptable salt thereof) may be contained in an amount of 0.1 parts by weight to 15 parts by weight, and more specifically 3 parts by weight to 10 parts by weight, based on 100 parts by weight of the total composite preparation, but the amount is not limited thereto. Additionally, the second active ingredient may be contained in an amount of 1 part by weight to 20 parts by weight, and more specifically 5 parts by weight to 15 parts by weight, based on 55 parts by weight of the second composition.

The excipient may be contained in the second active ingredient in an amount of 1 part by weight to 25 parts by weight, and specifically 10 parts by weight to 20 parts by weight, based on 100 parts by weight of the total composite preparation. Additionally, the excipient may be contained in an amount of 20 parts by weight to 50 parts by weight, and more specifically 25 parts by weight to 40 parts by weight, based on 55 parts by weight of the second composition.

The coating agent may be contained in the second active ingredient in an amount of 0.5 parts by weight to 10 parts by weight, and specifically 1 part by weight to 5 parts by weight, based on 100 parts by weight of the total composite preparation. Additionally, the coating agent may be contained in an amount of 1 part by weight to 10 parts by weight, and more specifically 3 parts by weight to 8 parts by weight, based on 55 parts by weight of the second composition.

The enteric-coating agent may be contained in the second active ingredient in an amount of 0.1 parts by weight to 10 parts by weight, and specifically 1 part by weight to 7 parts by weight, based on 100 parts by weight of the total composite preparation. Additionally, the enteric-coating agent may be contained in an amount of 1 part by weight to 20 parts by weight, and more specifically 5 parts by weight to 15 parts by weight, based on 55 parts by weight of the second composition.

When the second composition containing rabeprazole or a salt thereof is used as an enteric-coated pellet, an excipient such as talc and/or titanium oxide may be contained therein. The talc and titanium oxide may be contained in an amount of 0.01 parts by weight to 3 parts by weight, and more specifically 0.1 parts by weight to 1 part by weight, based on 100 parts by weight of the total composite preparation. Additionally, the alkalifying agent may be contained in an amount of 0.05 parts by weight to 3.0 parts by weight, and more specifically 0.1 parts by weight to 2.0 parts by weight, based on 55 parts by weight of the second composition.

According to an embodiment of the present invention, the composite preparation of the present invention may be prepared according to the method for preparing a composite preparation including:

i) preparing an enteric-coated tablet containing rabeprazole or a pharmaceutically acceptable salt thereof, excipient, coating agent, and enteric-coating agent;

ii) preparing a rapid-release tablet containing mosapride or a pharmaceutically acceptable salt thereof;

iii) preparing a suspended-release tablet containing mosapride or a pharmaceutically acceptable salt thereof and a release-controlling agent; and iv) filling the rapid-release tablet, suspended-release tablet, and enteric-coated pellet into a capsule.

In the above preparation method, the products of steps i) to iii) may be prepared in any order and these products may be produced simultaneously.

The composite preparation of the present invention may be administered before or after a meal, but it is generally administered on an empty stomach before a meal to be less affected by the food being consumed.

The composite preparation of the present invention may be effective in the prevention, treatment, or amelioration of gastrointestinal disorders and may also be useful in the improvement of gastrointestinal symptoms.

The gastrointestinal disorders, which are also called by various names, such as chronic dyspepsia, non-ulcerative dyspepsia, chronic diarrhea, irritable bowel, irritable enteritis, chronic gastritis, chronic abdominal pain, neurogenic gastroenteritis, etc., are diseases that accompany symptoms, such as gastrointestinal pain, constipation, diarrhea, vomiting, etc., and as examples, various symptoms that occur in the gastrointestinal tract, but the kinds of the symptoms are not limited thereto. Additionally, the gastrointestinal symptoms include dyspepsia, and these symptoms may specifically be based on the Rome Criteria, and more specifically functional dyspepsia classified according to the Rome III Diagnostic Criteria for Functional Gastrointestinal Disorders, but the symptoms are not limited thereto.

Since the composite preparation of the present invention can greatly reduce the amount of an excipient to be contained therein, it is advantageous in that the preparation can be prepared in a smaller size despite the fact that it is a composite preparation, thereby improving drug compliance of patients and cost effectiveness. According to an embodiment of the present invention, the total weight of the composite preparation of the present invention may be 500 mg or less, preferably 400 mg or less, more preferably 300 mg or less, and most preferably 210 mg or less.

Additionally, the composite preparation of the present invention is prepared as a sustained-release or suspended-release layer using a mosapride composition together with a release-controlling agent, the active ingredient and the active metabolite can be continuously maintained at a constant level in the blood plasma. As a result, the composite preparation of the present invention has advantages in that not only can it significantly increase convenience in drug administration by reducing the administration frequencies and increase drug compliance of patients by increasing their drug adaptability, but it also can introduce a synergic effect and an economic effect according to the combined administration of rabeprazole inhibiting gastric acid secretion.

DETAILED DESCRIPTION OF THE INVENTION

Hereinafter, the present invention will be described in more detail with reference to the following Examples.

However, these Examples are for illustrative purposes only and the invention is not limited by these Examples.

1. Examples 1 to 3: Preparation of Composite Preparation of Suspended-Release Mosapride Tablet Containing Rabeprazole Core Tablet (Core Tablet)

1-1. Preparation of Enteric-Coated Rabeprazole Tablet

According to the ingredients and amounts listed in the inner core tablet of Table 1 below, rabeprazole sodium, D-mannitol, magnesium oxide, low-substituted HPC (L-HPC), and crospovidone were mixed. A solution, which was prepared in advance by dissolving hydroxypropyl cellulose (hereinafter, HPC) in ethanol, was added to the mixture and kneaded and granulated, and dried in a cabinet dryer at between 50° C. and 60° C. for 1 to 2 hours (to 2% or less of LOD). The resultant was prepared into particles and mixed with sodium stearyl fumarate, a glidant. The mixture was tableted (120 mg/tablet), and film-coated by a conventional method using ACRYL-EZE® II (a commercial product of Colorcone, Co., Ltd.) (i.e., an enteric-coating agent) to prepare an enteric-coated rabeprazole tablet containing 10 mg of rabeprazole sodium per tablet.

1-2. Preparation of Granulated Product of Rapid-Release Layer Containing Mosapride According to the ingredients and amounts listed in the outer layer and rapid-release layer of Table 1 below, mosapride citrate dihydrate, microcrystalline cellulose, lactose hydrate, and low-substituted L-HPC were mixed. A solution, which was prepared in advance by dissolving povidone K-30 in ethanol, was added to the mixture and kneaded and granulated, and dried in a cabinet dryer at between 50° C. and 60° C. for 1 to 2 hours (to 2% or less of LOD). The resultant was prepared into particles and mixed with the remaining glidant.

1-3. Preparation of Granulated Product of Suspended-Release Layer Containing Mosapride According to the ingredients and amounts listed in the suspended-release layer of the outer layer of Table 1 below, mosapride citrate dihydrate, microcrystalline cellulose, lactose hydrate, low-viscosity HPMC (4000 cps, HPMC 2910), high-viscosity HPMC (100,000 cps, HPMC 2208), and low-substituted L-HPC were mixed. A solution, which was prepared in advance by dissolving povidone K-30 in ethanol, was added to the mixture and kneaded and granulated, and dried in a cabinet dryer at between 50° C. and 60° C. for 1 to 2 hours (to 2% or less of LOD). The resultant was prepared into particles and mixed with the remaining glidant.

1-4. Preparation of Composite Preparation of Suspended-Release Mosapride Tablet Containing Rabeprazole Core Tablet The enteric-coated rabeprazole tablets (130.0 mg/tablet) prepared according to Table 1 below were used as an inner core. The enteric-coated rabeprazole tablets were supplied as inner core tablets into an inner core supplier of a core tablet tableting machine (Kilian type). Mosapride granules of a rapid-release part were supplied to a granule supplier of a first outer layer in an amount of 150.0 mg per tablet according to Examples of Table 1 and mosapride granules of a suspended-release part were supplied to a granule supplier of a second outer layer in an amount of 150.0 mg per tablet according to Examples of Table 1, and tableted into core tablets. Opadry-OY-C-7000A (a commercial product of Colorcone, Co., Ltd.), which is a film-coating agent, was dispersed or dissolved in ethanol to prepare a coating solution. The above core tablets were added into the coating machine SFC-30 (Sejong Machinery, Korea). A schematic diagram of the formulation of the core tablet is shown in FIG. 1.

TABLE 1

| Category | Ingredients | Active Ingredient | Example 1 | Example 2 | Example 3 |
|---|---|---|---|---|---|
| Inner Core Tablet | Active Ingredient | rabeprazole sodium | 10.00 | 10.00 | 10.00 |
| | Excipient | D-mannitol | 44.00 | 44.00 | 44.00 |
| | Alkalifying Agent | magnesium oxide | 45.00 | 45.00 | 45.00 |
| | Binder | HPC | 3.00 | 3.00 | 3.00 |
| | Disintegrant | L-HPC | 12.00 | 12.00 | 12.00 |
| | Disintegrant | crospovidone | 3.00 | 3.00 | 3.00 |
| | Glidant | sodium stearyl fumarate | 3.00 | 3.00 | 3.00 |
| | Enteric-coating Agent | ACRYL-EZE ®II | 10.00 | 10.00 | 10.00 |
| | Subtotal of inner core tablet (mg/tablet) | | 130 | 130 | 130 |
| Outer Layer | Active Ingredient | mosapride citrate dihydrate | 5.29 | 5.29 | 5.29 |
| | Excipient | microcrystalline cellulose | 47.29 | 47.29 | 47.29 |
| | Excipient | lactose hydrate | 37.52 | 37.52 | 37.52 |
| | Disintegrant | L-HPC | 48 | 48 | 48 |
| | Binder | povidone K-30 | 10 | 10 | 10 |
| | Glidant | light anhydrous silicic acid | 0.66 | 0.66 | 0.66 |
| | Glidant | magnesium stearate | 1.24 | 1.24 | 1.24 |
| | Subtotal of rapid-release part (mg/tablet) | | 150 | 150 | 150 |
| Outer Layer | Active Ingredient | mosapride citrate dihydrate | 10.58 | 10.58 | 10.58 |
| | Excipient | microcrystalline cellulose | 26 | 26 | 26 |
| | Excipient | lactose hydrate | 29.56 | 29.56 | 29.56 |
| | Sustained-release Agent | low-viscosity HPMC (HPMC 2910) | 16 | 18 | 20 |
| | Sustained-release Agent | high-viscosity HPMC (HPMC 2208) | 28 | 26 | 24 |
| | Binder | povidone K-30 | 10 | 10 | 10 |

TABLE 1-continued

| Category | Ingredients | Active Ingredient | Example 1 | Example 2 | Example 3 |
|---|---|---|---|---|---|
| | Disintegrant | L-HPC | 28 | 28 | 28 |
| | Glidant | light anhydrous silicic acid | 0.62 | 0.62 | 0.62 |
| | Glidant | magnesium stearate | 1.24 | 1.24 | 1.24 |
| | Subtotal of suspended-release part (mg/tablet) | | 150 | 150 | 150 |
| | Coating Agent | Opadry-OY-C-7000A | 5 | 5 | 5 |
| Core Tablet | | Total (mg/tablet) | 435 | 435 | 435 |

1-5. Results of In Vitro Test

Figure 5:
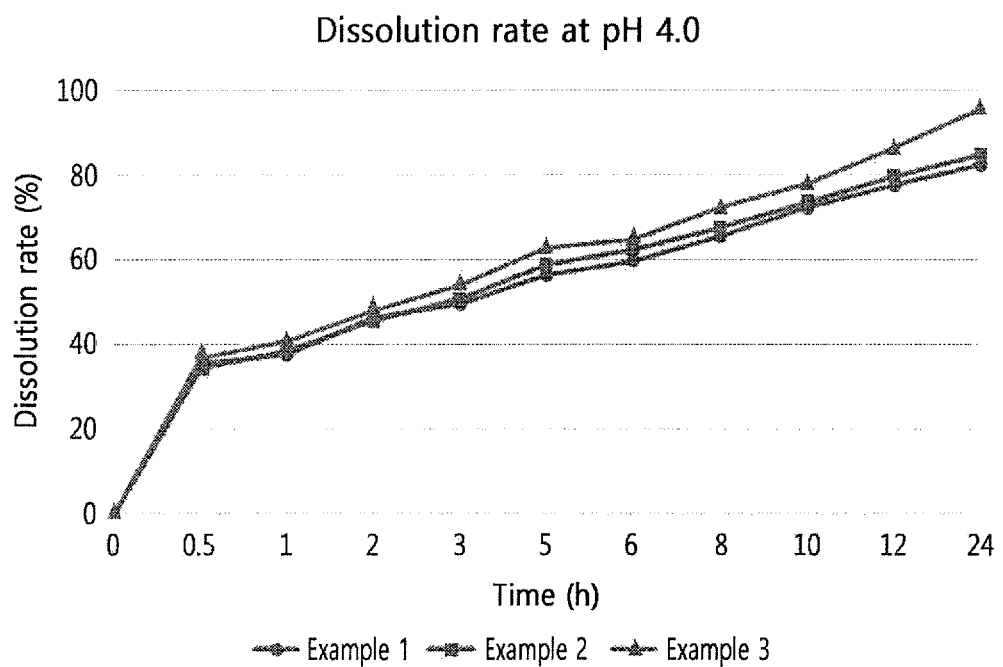
FIG. 5 is a graph showing the change in average dissolution rate over time of tablet core-containing composite preparations prepared according to Examples 1 to 3.

Dissolution rate tests were performed in vitro with respect to the core tablets of Examples 1 to 3 in Table 1. Dissolution features of mosapride citrate dihydrate suspended-release tablet preparation as an active ingredient according to time in a dissolution medium (the Korean Pharmacopoeia) at pH 4.0 were confirmed, and the results are shown in Table 2 below and FIG. 5.

Detailed conditions of the dissolution test are as follows.
Subject: Core tablet preparations of Examples 1 to 3 in Table 1
Dissolution test medium: disintegration test of the Korean Pharmacopoeia at pH 4.0
Volume of dissolution medium: 900 mL, test temperature: 37±0.5° C.
Test method: the second method of dissolution test (paddle method) of the Korean Pharmacopoeia (50 revolutions/min)
Sample collection: Eluates are collected at each sample collection time and filtered with a 0.45 μm filter to prepare a sample solution. After collection of each eluate, an equal amount of a fresh dissolution medium is replenished thereto for calibration purposes.
Analysis equipment: ultraviolet spectrophotometer (UV-Vis), absorbance at 273 nm longer than 24 hours. Accordingly, it can be seen that the sustained-release tablet of the present invention can be easily controlled with regard to its dissolution feature according to the amount of the hydrophilic polymer of high-viscosity HPMC to low-viscosity HPMC contained therein.

2. Examples 4 and 5: Preparation of Composite Preparation Containing Enteric-Coated Rabeprazole Tablet and Triple-Layer Mosapride Tablet

2-1. Preparation of Enteric-Coated Rabeprazole Tablet

According to the ingredients and amounts listed in the enteric-coated tablets of Table 3 below, rabeprazole sodium, D-mannitol, magnesium oxide, and low-substituted HPC (L-HPC), crospovidone were mixed. A solution, which was prepared in advance by dissolving HPC in ethanol, was added to the mixture and kneaded and granulated, and dried in a cabinet dryer at between 50° C. and 60° C. for 1 to 2 hours (to 2% or less of LOD). The resultant was prepared into particles and mixed with sodium stearyl fumarate, a glidant. The mixture was tableted (120 mg/tablet), and film-coated by a conventional method using ACRYL-EZE® II (a commercial product of Colorcone, Co., Ltd.) (i.e., an

TABLE 2

| | Average dissolution rate in dissolution test medium at pH 4.0 (%) | | | | | | | | | |
|---|---|---|---|---|---|---|---|---|---|---|
| Category | 0.5 Hours | 1 Hour | 2 Hours | 3 Hours | 5 Hours | 6 Hours | 8 Hours | 10 Hours | 12 Hours | 24 Hours |
| Example 1 | 35.5 | 37.4 | 46.5 | 49.5 | 56.3 | 59.5 | 65.4 | 72.4 | 77.5 | 82.1 |
| Example 2 | 34.4 | 38.5 | 45.6 | 50.8 | 58.6 | 62.4 | 67.5 | 73.5 | 79.3 | 84.6 |
| Example 3 | 36.8 | 40.9 | 48.1 | 53.9 | 62.5 | 64.8 | 72.3 | 77.9 | 86.4 | 95.6 |

Considering the dissolution rates with time shown in Table 2, all of the mosapride citrate hydrate sustained-release tablets showed 24-hour dissolution rates of 80% or higher, and they showed a characteristic of continuously releasing an active ingredient, and in particular, the sustained-release tablet of Example 3 was found to have a dissolution rate of greater than 95% at 24 hours, confirming that the tablet has a very suitable dissolution feature for once-daily administration. Meanwhile, in the cases of Examples 1 and 2, the weight ratio of the high-viscosity HPMC (HPMC 2208) was relatively high among the sustained-release agents compared to the drugs of an active ingredient, thus confirming that the tablet has a dissolution profile of suspended release having a dissolution rate of enteric-coating agent) to prepare an enteric-coated rabeprazole tablet containing 10 mg of rabeprazole sodium per tablet.

2-2. Preparation of Granulated Products of First and Third Rapid-Release Layers Containing Mosapride According to the ingredients and amounts listed in the rapid-release layer in the triple-layer tablets of Table 3 below, mosapride citrate dihydrate, microcrystalline cellulose, lactose hydrate, and low-substituted HPC (L-HPC) were mixed. A solution, which was prepared in advance by dissolving povidone K-30 in ethanol, was added to the mixture and kneaded and granulated, and dried in a cabinet dryer at between 50° C. and 60° C. for 1 to 2 hours (to 2% or less of LOD). The resultant was prepared into particles and mixed with the remaining glidant.

2-3. Preparation of Granulated Product of Second Suspended-Release Layer Containing Mosapride According to the ingredients and amounts listed in the suspended-release layer in the triple-layer tablets of Table 3 below, mosapride citrate dihydrate microcrystalline cellulose, lactose hydrate, low-viscosity HPMC (4000 cps, HPMC 2910), high-viscosity HPMC (100,000 cps, HPMC 2208), and low-substituted HPC (L-HPC) were mixed. A solution, which was prepared in advance by dissolving povidone K-30 in ethanol, was added to the mixture and kneaded and granulated, and dried in a cabinet dryer at between 50° C. and 60° C. for 1 to 2 hours (to 2% or less of LOD). The resultant was prepared into particles and mixed with the remaining glidant.

2.4. Preparation of Composite Preparation Containing Enteric-Coated Rabeprazole Tablet and Triple-Layer Suspended-Release Mosapride Tablet A triple-layer mosapride tablet was prepared using the granulated products of a first to third rapid-release and suspended-release layers of mosapride prepared according to Examples of Table 3 below. The granulated products of the first rapid-release layer, the second suspended-release layer, and the third rapid-release layer were sequentially filled in this order to contain a weight of 225.0 mg per tablet, and tableted using a tableting machine for triple-layer tablets, and triple-layer tablets were prepared to have a final hardness of 10 MPa to 14 MPa by allowing them to undergo pre-pressure and main-pressure. The thus-prepared triple-layer mosapride tablets and the enteric-coated rabeprazole tablets prepared previously were filled into hard capsules of size 0 to 2 in this order, and thereby enteric-coated rabeprazole tablets and triple-layer suspended-release mosapride tablets were prepared. The schematic diagram of the formulation of the composite preparation is shown in FIG. 2.

TABLE 3

| Category | Ingredients | Active Ingredient | Example 4 | Example 5 |
|---|---|---|---|---|
| Enteric-coated Tablet | Active Ingredient | rabeprazole sodium | 10 | 10 |
| | Excipient | D-mannitol | 44 | 29 |
| | Alkalifying Agent | magnesium oxide | 45 | 30 |
| | Binder | HPC | 3 | 3 |
| | Disintegrant | L-HPC | 12 | 12 |
| | Disintegrant | crospovidone | 3 | 3 |
| | Glidant | sodium stearyl fumarate | 3 | 3 |
| | Enteric-coating Agent | ACRYL-EZE ® | 10 | 10 |
| | Subtotal of enteric-coated tablet (mg/tablet) | | 130 | 100 |
| First Rapid-release Layer | Active Ingredient | mosapride citrate dihydrate | 2.645 | 2.645 |
| | Excipient | microcrystalline cellulose | 21 | 21 |
| | Excipient | lactose hydrate | 21.405 | 21.405 |
| | Disintegrant | L-HPC | 24 | 24 |
| | Binder | povidone K-30 | 5 | 5 |
| | Glidant | light anhydrous silicic acid | 0.33 | 0.33 |
| | Glidant | magnesium stearate | 0.62 | 0.62 |
| | Subtotal of rapid-release part (mg/tablet) | | 75 | 75 |
| Second Suspended-release Layer | Active Ingredient | mosapride citrate dihydrate | 10.58 | 10.58 |
| | Excipient | microcrystalline cellulose | 13 | 13 |
| | Excipient | lactose hydrate | 9.49 | 9.49 |
| | Sustained-release Agent | low-viscosity HPMC (HPMC 2910) | 8 | 8 |
| | Sustained-release Agent | high-viscosity HPMC (HPMC 2208) | 14 | 14 |
| | Binder | povidone K-30 | 5 | 5 |
| | Disintegrant | L-HPC | 14 | 14 |
| | Glidant | light anhydrous silicic acid | 0.31 | 0.31 |
| | Glidant | magnesium stearate | 0.62 | 0.62 |
| | Subtotal of suspended-release part (mg/tablet) | | 75 | 75 |
| Third Rapid-release Layer | Active Ingredient | mosapride citrate dihydrate | 2.645 | 2.645 |
| | Excipient | microcrystalline cellulose | 21 | 21 |
| | Excipient | lactose hydrate | 21.405 | 21.405 |
| | Disintegrant | L-HPC | 24 | 24 |
| | Binder | povidone K-30 | 5 | 5 |
| | Glidant | light anhydrous silicic acid | 0.33 | 0.33 |
| | Glidant | magnesium stearate | 0.62 | 0.62 |
| | Subtotal of rapid-release part (mg/tablet) | | 75 | 75 |
| Triple-layer Tablet | | Subtotal of triple-layer tablet (mg/tablet) | 225 | 225 |
| Composite Preparation | | Total (mg/tablet) | 355 | 325 |

2-5. Results of In Vitro Test

Dissolution rate tests were performed in vitro with respect to the composite preparations containing a triple-layer tablet of Examples 4 and 5 in Table 3. Dissolution features of the mosapride citrate dihydrate suspended-release tablet preparation as an active ingredient according to time in a dissolution medium (the Korean Pharmacopoeia) at pH 4.0 were confirmed, and the results are shown in Table 4 below.

Detailed conditions of the dissolution test are as follows.
Subject: Triple-tablet-containing composite preparations of Examples 4 and 5 in Table 3
Dissolution test medium: disintegration test of the Korean Pharmacopoeia at pH 4.0
Volume of dissolution medium: 900 mL, test temperature: 37±0.5° C.
Test method: the second method of dissolution test (paddle method) of the Korean Pharmacopoeia (50 revolutions/min)
Sample collection: Eluates are collected at each sample collection time and filtered with a 0.45 µm filter to prepare a sample solution. After collection of each eluate, an equal amount of a fresh dissolution medium is replenished thereto for calibration purposes.
Analysis equipment: ultraviolet spectrophotometer (UV-Vis), absorbance at 273 nm

TABLE 4

| Category | Average dissolution rate in dissolution test medium at pH 4.0 (%) | | | | | | | | | |
| --- | --- | --- | --- | --- | --- | --- | --- | --- | --- | --- |
| | 0.5 Hours | 1 Hour | 2 Hours | 3 Hours | 5 Hours | 6 Hours | 8 Hours | 10 Hours | 12 Hours | 24 Hours |
| Example 4 | 32.3 | 39.5 | 47.1 | 53.2 | 62.5 | 68.8 | 72.3 | 77.9 | 86.4 | 95.6 |
| Example 5 | 33.4 | 38.2 | 46.6 | 52.6 | 60.6 | 69.4 | 73.5 | 79.5 | 85.3 | 96.3 |

Considering the dissolution rates with time shown in Table 4, the mosapride citrate hydrate of both composite preparations of Examples 4 and 5 showed no significant difference in dissolution features compared to the double-layer mosapride tablet of the present invention, and both composite preparations showed a characteristic of suspended release by continuously releasing an active ingredient. In addition, both composite preparations of Examples 4 and 5 were shown to have a hardness of about 10 MPa to 14 MPa, and the tablets were disintegrated within 10 minutes in a disintegration test, thus confirming that there was also no significant difference with respect to physicochemical characteristics.

In particular, in the case of the composite preparation of Example 5, the rabeprazole-containing tablet did not show any problem with regard to the tableting process even though the amounts of D-mannitol (an excipient) and magnesium oxide (an alkalifying agent) were partially reduced. Additionally, due to the decrease in the amount of the excipient, the composite preparation was more easily filled into hard capsule No. 2, compared to that of the composite preparation of Example 4, which was suitable to be filled into hard capsule No. 0, being smaller in size than hard capsule No. 2. When the hard capsule number of a drug is large or the capsule size of a drug is small, it has an advantage in developing drugs because these small-sized drugs help patients to take medicine and are thus more preferred, thereby increasing drug compliance of patients.

3. Examples 6 and 7: Preparation of Composite Preparation of Rapid-Release Mosapride Tablet, Suspended-Release Mosapride Tablet, and Enteric-Coated Rabeprazole Tablet (Composite Tablet)

3-1. Preparation of Enteric-Coated Rabeprazole Tablet

According to the ingredients and amounts listed in the enteric-coated tablets of Table 5 below, rabeprazole sodium, D-mannitol, magnesium oxide, low-substituted HPC (L-HPC), and crospovidone were mixed. A solution, which was prepared in advance by dissolving HPC in ethanol, was added to the mixture and kneaded and granulated, and dried in a cabinet dryer at between 50° C. and 60° C. for 1 to 2 hours (to 2% or less of LOD). The resultant was prepared into particles and mixed with sodium stearyl fumarate, a glidant. The mixture was tableted (120 mg/tablet), and film-coated by a conventional method using ACRYL-EZE® II (a commercial product of Colorcone, Co., Ltd.) (i.e., an enteric-coating agent) to prepare an enteric-coated rabeprazole tablet containing 10 mg of rabeprazole sodium per tablet.

3-2. Preparation of Rapid-Release Mosapride Tablet

According to the ingredients and amounts listed in the rapid-release tablets of Table 5 below, mosapride citrate dehydrate, microcrystalline cellulose, lactose hydrate, and low-substituted HPC (L-HPC) were mixed. A solution, which was prepared in advance by dissolving povidone K-30 in ethanol, was added to the mixture and kneaded and granulated, and dried in a cabinet dryer at between 50° C. and 60° C. for 1 to 2 hours (to 2% or less of LOD). The resultant was prepared into particles and mixed with the remaining glidant. The mixture was tableted by a conventional tableting method to prepare tablets having a weight of 75 mg per tablet and a hardness of 10 MPa to 14 MPa, and thereby rapid-release tablets containing mosapride citrate hydrate were prepared.

3-3. Preparation of Suspended-Release Mosapride Tablet

According to the amounts of the ingredients listed in the suspended-release tablets of Table 5 below, mosapride citrate dehydrate, microcrystalline cellulose, lactose hydrate, low-viscosity HPMC (4000 cps, HPMC 2910), high-viscosity HPMC (100,000 cps, HPMC 2208), and low-substituted HPC (L-HPC) were mixed. A solution, which was prepared in advance by dissolving povidone K-30 in ethanol, was added to the mixture and kneaded and granulated, and dried in a cabinet dryer at between 50° C. and 60° C. for 1 to 2 hours (to 2% or less of LOD). The resultant was prepared into particles and mixed with the remaining glidant. The mixture was tableted by a conventional tableting method to prepare tablets having a weight of 75 mg per tablet and a hardness of 10 MPa to 14 MPa, and thereby suspended-layer tablets containing mosapride citrate hydrate were prepared.

3-4. Preparation of Composite Preparation of Rapid-Release Mosapride Tablet, Suspended-Release Mosapride Tablet, and Enteric-Coated Rabeprazole Tablet The rapid-release mosapride tablets, suspended-release mosapride tablets, and enteric-coated tablets prepared according to Table 5 below were sequentially filled using an apparatus for preparing hard capsule composite preparations. The preparations were filled into hard capsules (Capsule Nos. 0 to 2), and thereby a composite preparation containing the rapid-release mosapride tablet, suspended-release mosapride tablet, and enteric-coated tablet was prepared. The schematic drawing of the formulation of the composite preparations is shown in

TABLE 5

| Category | Ingredients | Active Ingredient | Example 6 | Example 7 |
|---|---|---|---|---|
| Enteric-coated Tablet | Active Ingredient | rabeprazole sodium | 10 | 10 |
| | Excipient | D-mannitol | 44 | 29 |
| | Alkalifying Agent | magnesium oxide | 45 | 30 |
| | Binder | HPC | 3 | 3 |
| | Disintegrant | L-HPC | 12 | 12 |
| | Disintegrant | crospovidone | 3 | 3 |
| | Glidant | sodium stearyl fumarate | 3 | 3 |
| | Enteric-coating Agent | ACRYL-EZE ® | 10 | 10 |
| | Subtotal of enteric-coated tablet (mg/tablet) | | 130 | 100 |
| Rapid-release Tablet | Active Ingredient | mosapride citrate dihydrate | 5.29 | 5.29 |
| | Excipient | microcrystalline cellulose | 21 | 21 |
| | Excipient | lactose hydrate | 18.76 | 18.76 |
| | Disintegrant | L-HPC | 24 | 24 |
| | Binder | povidone K-30 | 5 | 5 |
| | Glidant | light anhydrous silicic acid | 0.33 | 0.33 |
| | Glidant | magnesium stearate | 0.62 | 0.62 |
| | Subtotal of rapid-release tablet (mg/tablet) | | 75 | 75 |
| Suspended-release Tablet | Active Ingredient | mosapride citrate dihydrate | 10.58 | 10.58 |
| | Excipient | microcrystalline cellulose | 13 | 13 |
| | Excipient | lactose hydrate | 9.49 | 9.49 |
| | Sustained-release Agent | low-viscosity HPMC (HPMC 2910) | 8 | 8 |
| | Sustained-release Agent | high-viscosity HPMC (HPMC 2208) | 14 | 14 |
| | Binder | povidone K-30 | 5 | 5 |
| | Disintegrant | L-HPC | 14 | 14 |
| | Glidant | light anhydrous silicic acid | 0.31 | 0.31 |
| | Glidant | magnesium stearate | 0.62 | 0.62 |
| | Subtotal of suspended-release tablet (mg/tablet) | | 75 | 75 |
| Composite Preparation | Total (mg/tablet) | | 280 | 250 |

3-5. Results of In Vitro Test

Dissolution rate tests were performed in vitro with respect to the composite preparations of Examples 6 and 7 in Table 5. Dissolution features of the mosapride citrate dihydrate suspended-release tablet preparation as an active ingredient according to time in a dissolution medium (the Korean Pharmacopoeia) at pH 4.0 were confirmed, and the results are shown in Table 6 below.

Detailed conditions of the dissolution test are as follows.

Subject: Composite preparations of Examples 6 and 7 in Table 5

Dissolution test medium: disintegration test of the Korean Pharmacopoeia at pH 4.0

Volume of dissolution medium: 900 mL, test temperature: 37±0.5° C.

Test method: the second method of dissolution test (paddle method) of the Korean Pharmacopoeia (50 revolutions/min)

Sample collection: Eluates are collected at each sample collection time and filtered with a 0.45 μm filter to prepare a sample solution. After collection of each eluate, an equal amount of a fresh dissolution medium is replenished thereto for calibration purposes.

Analysis equipment: ultraviolet spectrophotometer (UV-Vis), absorbance at 273 nm

TABLE 6

| | Average dissolution rate in dissolution test medium at pH 4.0 (%) | | | | | | | | | |
|---|---|---|---|---|---|---|---|---|---|---|
| Category | 0.5 Hours | 1 Hour | 2 Hours | 3 Hours | 5 Hours | 6 Hours | 8 Hours | 10 Hours | 12 Hours | 24 Hours |
| Example 6 | 31.5 | 38.4 | 46.1 | 52.3 | 61.5 | 69.8 | 73.3 | 79.9 | 85.4 | 96.8 |
| Example 7 | 32.2 | 37.3 | 45.6 | 53.9 | 60.8 | 68.4 | 74.5 | 78.5 | 86.2 | 97.3 |

Considering the dissolution rates with time shown in Table 6, the mosapride citrate hydrate of both composite preparations of Examples 6 and 7 showed no significant difference in dissolution features compared to the double-layer mosapride tablet of the present invention, and both composite preparations showed a characteristic of suspended release by continuously releasing an active ingredient for 24 hours. In addition, both composite preparations of Examples 4 and 5 were shown to have a hardness of about 10 MPa to 14 MPa, and the tablets were disintegrated within 10 minutes in a disintegration test, thus confirming that there was also no significant difference with respect to physicochemical characteristics.

In particular, in the case of the composite preparation of Example 7, the rabeprazole-containing tablet did not show any problem with regard to the tableting process even though the amounts of D-mannitol (an excipient) and magnesium oxide (an alkalifying agent) were partially reduced. Additionally, due to the decrease in the amount of the excipient, the composite preparation was more easily filled into hard capsule No. 2, compared to that of the composite preparation of Example 6, which was suitable to be filled into hard capsule No. 0, being smaller in size than hard capsule No. 2. When the hard capsule number of a drug is large or the capsule size of a drug is small, it has an advantage in developing drugs because these small-sized drugs help patients to take medicine and are thus more preferred, thereby increasing drug compliance of patients.

4. Examples 8 and 9: Preparation of Composite Preparation of Rapid-Release Mosapride Tablet, Suspended-Release Mosapride Table, and Enteric-Coated Rabeprazole Pellet (Composite Tablet Granules)

4-1. Preparation of Enteric-Coated Rabeprazole Pellet

According to the ingredients and amounts listed in the enteric-coated tablets of Table 7 below, a primary coating solution, which was prepared by mixing rabeprazole sodium, HPMC, PEG, and talc, and then mixed with a solution prepared in advance by dissolving titanium oxide in ethanol, was coated on spherical white sugar using a fluidized-bed coating apparatus at 60° C. to 70° C. with 40% relative humidity; followed by a second coating with a second coating solution, which was prepared by mixing a mixture of HPMC phthalate (HPMCP), PEG, and talc, with a solution prepared by dissolving titanium oxide in ethanol; and the resultant was dried for 30 minutes to prepare an enteric-coated rabeprazole pellet.

4-2. Preparation of Rapid-Release Mosapride Tablet

According to the ingredients and amounts listed in the rapid-release tablets of Table 7 below, mosapride citrate dehydrate, microcrystalline cellulose, lactose hydrate, and low-substituted HPC (L-HPC) were mixed. A solution, which was prepared in advance by dissolving povidone K-30 in ethanol, was added to the mixture and kneaded and granulated, and dried in a cabinet dryer at between 50° C. and 60° C. for 1 to 2 hours (to 2% or less of LOD). The resultant was prepared into particles and mixed with the remaining glidant. The mixture was tableted by a conventional tableting method to prepare tablets having a weight of 75 mg per tablet and a hardness of 10 MPa to 14 MPa, and thereby rapid-release tablets containing mosapride citrate hydrate were prepared.

4-3. Preparation of Suspended-Release Mosapride Tablet

According to the ingredients and amounts listed in the suspended-release tablets of Table 7 below, mosapride citrate dehydrate, microcrystalline cellulose, lactose hydrate, low-viscosity HPMC (4,000 cps, HPMC 2910), high-viscosity HPMC (100,000 cps, HPMC 2208), and low-substituted HPC (L-HPC) were mixed. A solution, which was prepared in advance by dissolving povidone K-30 in ethanol, was added to the mixture and kneaded and granulated, and dried in a cabinet dryer at between 50° C. and 60° C. for 1 to 2 hours (to 2% or less of LOD). The resultant was prepared into particles and mixed with the remaining glidant. The mixture was tableted by a conventional tableting method to prepare tablets having a weight of 75 mg per tablet and a hardness of 10 MPa to 14 MPa, and thereby suspended-release tablets containing mosapride citrate hydrate were prepared.

4-4. Preparation of Composite Preparation of Rapid-Release Mosapride Tablet, Suspended-Release Mosapride Tablet, and Enteric-Coated Rabeprazole Pellet The rapid-release mosapride tablets, suspended-release mosapride tablets, and enteric-coated tablets prepared according to Table 7 below were sequentially filled using an apparatus for preparing hard capsule composite preparations. The preparations were filled into hard capsules (Capsule Nos. 0 to 2), and thereby a composite preparation containing the rapid-release mosapride tablet, suspended-release mosapride tablet, and enteric-coated tablet was prepared. The schematic drawing of the formulation of the composite preparations is shown in FIG. 4.

TABLE 7

| Category | Ingredients | Active Ingredient | Example 8 | Example 9 |
|---|---|---|---|---|
| Enteric-coated Pellet | Active Ingredient | rabeprazole sodium | 10 | 10 |
| | Excipient | white sugar | 30 | 30 |
| | Coating Agent | HPMC | 5 | 5 |
| | Enteric-coating Agent | HPMC phthalate (HPMCP) | 8 | 12 |
| | Excipient | polyethylene glycol (PEG) | 1 | 1 |
| | Excipient | talc | 0.5 | 1 |
| | Excipient | titanium oxide | 0.5 | 1 |
| | Subtotal of enteric-coated pellet (mg/tablet) | | 55 | 60 |
| Rapid-release Tablet | Active Ingredient | Mosapride citrate dihydrate | 5.29 | 5.29 |
| | Excipient | microcrystalline cellulose | 21 | 21 |
| | Excipient | lactose hydrate | 18.76 | 18.76 |
| | Disintegrant | L-HPC | 24 | 24 |
| | Binder | povidone K-30 | 5 | 5 |
| | Glidant | light anhydrous silicic acid | 0.33 | 0.33 |
| | Glidant | magnesium stearate | 0.62 | 0.62 |
| | Subtotal of rapid-release tablet (mg/tablet) | | 75 | 75 |
| Suspended-release Tablet | Active Ingredient | mosapride citrate dihydrate | 10.58 | 10.58 |
| | Excipient | microcrystalline cellulose | 13 | 13 |
| | Excipient | lactose hydrate | 9.49 | 9.49 |
| | Sustained-release Agent | low-viscosity HPMC (HPMC 2910) | 8 | 8 |
| | Sustained-release Agent | high-viscosity HPMC (HPMC 2208) | 14 | 14 |
| | Binder | povidone K-30 | 5 | 5 |
| | Disintegrant | L-HPC | 14 | 14 |
| | Glidant | light anhydrous silicic acid | 0.31 | 0.31 |
| | Glidant | magnesium stearate | 0.62 | 0.62 |
| | Subtotal of suspended-release tablet (mg/tablet) | | 75 | 75 |
| Composite Preparation | Total (mg/tablet) | | 205 | 210 |

4-5. Results of In Vitro Tests

Dissolution rate tests were performed in vitro with respect to the composite preparations of Examples 8 and 9 in Table 7. Dissolution features of the mosapride citrate dihydrate suspended-release preparation as an active ingredient according to time in a dissolution medium (the Korean Pharmacopoeia) at pH 4.0 were confirmed, and the results are shown in Table 8 below.

Detailed conditions of the dissolution test are as follows.
Subject: Composite preparations of Examples 8 and 9 shown in Table 7
Dissolution test medium: disintegration test of the Korean Pharmacopoeia at pH 4.0

Volume of dissolution medium: 900 mL, test temperature: 37±0.5° C.

Test method: the second method of dissolution test (paddle method) of the Korean Pharmacopoeia (50 revolutions/min)

Sample collection: Eluates are collected at each sample collection time and filtered with a 0.45 μm filter to prepare a sample solution. After collection of each eluate, an equal amount of a fresh dissolution medium is replenished thereto for calibration purposes.

Analysis equipment: ultraviolet spectrophotometer (UV-Vis), absorbance at 273 nm

TABLE 8

| | Average dissolution rate in dissolution test medium at pH 4.0 (%) | | | | | | | | | |
|---|---|---|---|---|---|---|---|---|---|---|
| Category | 0.5 Hours | 1 Hour | 2 Hours | 3 Hours | 5 Hours | 6 Hours | 8 Hours | 10 Hours | 12 Hours | 24 Hours |
| Example 8 | 33.7 | 37.4 | 45.1 | 53.2 | 60.3 | 65.5 | 72.1 | 78.9 | 86.4 | 95.1 |
| Example 9 | 34.2 | 39.3 | 44.6 | 54.6 | 61.9 | 67.3 | 73.2 | 79.5 | 87.2 | 96.2 |

Considering the dissolution rates with time shown in Table 8, the mosapride citrate hydrate of both composite preparations of Examples 8 and 9 showed no significant difference in dissolution features compared to the double-layer mosapride tablet of the present invention, and both composite preparations showed a characteristic of suspended release by continuously releasing an active ingredient for 24 hours. Additionally, the composite preparations of Examples 8 and 9 were easily filled into hard capsules (Capsule Nos. 0 to 2).

5. Results of In Vitro Dissolution Test of Enteric-Coated Rabeprazole Sodium Tablet or Pellet Dissolution rate tests were performed in vitro with respect to the composite preparations of the present invention. Dissolution features of the enteric-coated rabeprazole sodium tablet as another active ingredient according to time in a dissolution medium (the Korean Pharmacopoeia) at pH 9.0 were confirmed, and the results are shown in Table 9 below.

Detailed conditions of the dissolution test are as follows.

Subject: Enteric-coated rabeprazole sodium tablet or pellet within the composite preparations of Examples 1 to 9

Dissolution test medium: pH 9.0 (Boric acid (3.0915 g)+KCl (3.7275 g)+NaOH (0.832 g) based on 1 L of water)

Volume of dissolution medium: 900 mL, test temperature: 37:0.5° C.

Test method: the second method of dissolution test (paddle method) of the Korean Pharmacopoeia (50 revolutions/min)

Sample collection: Eluates are collected at each sample collection time and filtered with a 0.45 μm filter to prepare a sample solution.

Analysis equipment: ultraviolet spectrophotometer (UV-Vis), absorbance at 284 nm, cell 1.0 cm

TABLE 9

| Category | Average dissolution rate in dissolution test solution at pH 9.0 (%) | | |
|---|---|---|---|
| | 15 minutes | 30 minutes | 45 minutes |
| Examples 1 to 9 | 5.71 | 56.24 | 101.29 |

Conventionally, the rabeprazole sodium drug had a disadvantage in that when the drug is exposed to an acidic condition of pH 6.8 or below, it is degraded, thus lowering its stability. Accordingly, it was difficult to conduct a dissolution test for the rabeprazole sodium drug in general conditions. However, as shown in Table 9 above, the rabeprazole sodium drug has been shown to be highly stable in a condition of pH 9.0, thus confirming that it is possible to design the formulations of the rabeprazole sodium drug by conducting dissolution tests.

The invention claimed is:

1. A composite tablet preparation comprising:
 a first composition which comprises (a) mosapride or a pharmaceutically acceptable salt thereof as a first active ingredient and (b) a rapid-release part and a sustained-release part; and
 a second composition which comprises rabeprazole or a pharmaceutically acceptable salt thereof as a second active ingredient,
 wherein the composite preparation has a core tablet structure in which the second composition is present as an enteric-coated inner core and the first composition surrounds the inner core,
 wherein both the rapid-release part and the sustained-release part of the first composition are in the form of granules, and the sustained-release part comprises as a release-controlling agent, a mixture of high-viscosity hydroxypropyl methylcellulose having a viscosity of 80,000 cps to 120,000 cps and low-viscosity hydroxypropyl methylcellulose having a viscosity of 2,000 cps to 20,000 cps at a weight ratio in the range 2.5:1 to 1:1.

2. The composite tablet preparation of claim 1, wherein the rapid-release part comprises mosapride or a pharmaceutically acceptable salt thereof, an excipient, a disintegrant, a binder, and a glidant and the sustained-release part comprises mosapride or a pharmaceutically acceptable salt thereof, an excipient, a disintegrant, a release-controlling agent, a binder, and a glidant.

3. The composite tablet preparation of claim 1, wherein the composite preparation complies with the dissolution profile according to the second method of the dissolution test (paddle method) of the Korean Pharmacopoeia in that the mosapride or pharmaceutically acceptable salt thereof in the water eluent at 37° C. and pH 4.0 is released in the range of 25% to 45% of the total weight of the mosapride or pharmaceutically acceptable salt thereof in 1 hour, in the range of 60% to 80% of the total weight of the mosapride or pharmaceutically acceptable salt thereof in 8 hours, and at least 85% of the total weight of the mosapride or pharmaceutically acceptable salt thereof in 24 hours.

4. The composite tablet preparation of claim 3, wherein the release-controlling agent is obtained by mixing the high-viscosity hydroxypropyl methylcellulose and the low-viscosity hydroxypropyl methylcellulose at a weight ratio in the range of 1.2:1 to 1:1, and the composite preparation complies with the dissolution profile according to the second method of the dissolution test (paddle method) of the Korean Pharmacopoeia in that the mosapride or pharmaceutically acceptable salt thereof comprised in the water eluent at 37° C. and pH 4.0 is released in the range of 40% to 45% of the total weight of the first active ingredient in 1 hour, in the range of 70% to 75% of the total weight of the mosapride or pharmaceutically acceptable salt thereof in 8 hours, and at least 90% of the total weight of the mosapride or pharmaceutically acceptable salt thereof in 24 hours.

5. The composite tablet preparation of claim 1,
 wherein the first composition comprises a rapid-release part comprising mosapride or a pharmaceutically acceptable salt thereof, an excipient, a disintegrant, a binder, and a glidant; and a sustained-release part comprising mosapride or a pharmaceutically acceptable salt thereof, an excipient, a disintegrant, a release-controlling agent, a binder, and a glidant;
 the second composition comprises rabeprazole or a pharmaceutically acceptable salt thereof, an excipient, an alkalifying agent, a binder, a disintegrant, and a glidant;
 and the composite tablet preparation complies with the dissolution profile according to the second method of the dissolution test (paddle method) of the Korean Pharmacopoeia in that the mosapride or pharmaceutically acceptable salt thereof in the water eluent at 37° C. and pH 4.0 is released in the range of 25% to 45% of the total weight of the mosapride or pharmaceutically acceptable salt thereof in 1 hour, in the range of 60% to 80% of the total weight of the mosapride or a pharmaceutically acceptable salt thereof in 8 hours, and more than 80% of the total weight of the mosapride or pharmaceutically acceptable salt thereof in 24 hours.

* * * * *